United States Patent
Barnard et al.

(10) Patent No.: US 6,417,005 B1
(45) Date of Patent: Jul. 9, 2002

(54) COVALENTLY IMMOBILIZED FLUOROIONOPHORES AS OPTICAL ION SENSORS

(75) Inventors: Steven Mark Barnard, San Diego, CA (US); Adrian Waldner, Allschwil (CH); David Reinhoudt, Hengelo (NL); Joseph Berger, Muttenz (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/171,330

(22) PCT Filed: Apr. 4, 1997

(86) PCT No.: PCT/EP97/01695

§ 371 (c)(1),
(2), (4) Date: Dec. 7, 1998

(87) PCT Pub. No.: WO97/39337

PCT Pub. Date: Oct. 23, 1997

(30) Foreign Application Priority Data

Apr. 16, 1996 (CH) ................................................ 959/96

(51) Int. Cl.[7] ........................ G01N 33/20; G01N 21/64; C07D 219/08
(52) U.S. Cl. ........................ 436/73; 422/56; 422/82.05; 422/82.06; 422/82.07; 422/82.08; 436/79; 436/172; 546/102; 546/104
(58) Field of Search ............................ 436/73, 79, 172; 422/55, 56, 82.05, 82.06, 82.07, 82.08; 546/102, 104

(56) References Cited

U.S. PATENT DOCUMENTS

| | | | |
|---|---|---|---|
| 4,367,072 A | 1/1983 | Vögtle et al. | ............... 436/501 |
| 5,453,517 A | * 9/1995 | Kuhn et al. | ................. 549/227 |
| 5,464,587 A | 11/1995 | Lippitsch et al. | ........ 422/82.07 |
| 5,474,743 A | * 12/1995 | Trend et al. | ............. 422/82.07 |
| 5,852,126 A | * 12/1998 | Barnard et al. | ........... 525/326.3 |
| 5,922,612 A | * 7/1999 | Alder et al. | ................ 436/163 |

FOREIGN PATENT DOCUMENTS

| | | | |
|---|---|---|---|
| CA | 2119840 | * | 9/1994 |
| EP | 0484865 | | 5/1992 |
| WO | 89/00997 | | 2/1989 |
| WO | 94/04483 | | 3/1994 |
| WO | 95/29959 | * | 11/1995 |
| WO | 95/30148 | * | 11/1995 |

OTHER PUBLICATIONS

K. Iwamoto et al, J. Chem. Soc., Perkin Trans 1 1992, 1885–1887, Aug. 1992.*
H. Chawla et al, J. Indian Inst. Sci. 1994, 74, 515–518, May 1994.*
M. R. Weaver et al, Anal. Chem. 1989, 61, 1001–1010, May 1989.*
T. Jin et al, J. Chem. Soc., Chem. Commun. 1992, 499–501.*
H. M. Chawla et al. Indian J. Chem. 1993, 32B, 1162–1164, Nov. 1993.*
H.M. Chawla et al. Chem. Abstr. 1995, 123, 111807W, Aug. 1995.*
Toth, K. et al., "Chromogenic Calix[4]arene as Ionophore for Potentiometric and Optical Sensors," Talanta, vol. 41, No. 6, 1994, pp. 1041–1049.
Perez–Jimenez, C. et al., "New Fluoroionophores for Alkali–metal Cations Based on Tetrameric Calixarenes," Journal of Material Chemistry, vol. 4, No. 1, 1994, pp. 145–150.

* cited by examiner

*Primary Examiner*—Arlen Soderquist
(74) *Attorney, Agent, or Firm*—Wenderoth, Lind & Ponack, L.L.P.

(57) ABSTRACT

Fluoroionophores that are functionalised with reactive groups and correspond to the formula $I\text{---}R_1\text{---}F\text{---}R_2\text{---}G$, wherein I is a monovalen residue of an ionophore, wherein F is a divalent residue of a fluorophore, wherein G is a functional group and $R_1$ and $R_2$ are each independently of the other a direct bond or a bridging group. The fluoroionophores may be covalently bound to carrier materials and are used as active components in polymer membranes of optical sensors for the detection of ions. The sensors are distinguished by a long usable life and a high degree of sensitivity.

17 Claims, No Drawings

COVALENTLY IMMOBILIZED FLUOROIONOPHORES AS OPTICAL ION SENSORS

This application is a 371 application of PCT/EP97/01695 filed Apr. 4, 1997.

The present invention relates to fluoroionophores that are covalently bound to organic or inorganic materials either directly or via a bridging group, and to processes for their preparation. The invention relates also to a) a sensor for determining ions, polar substances or lipophilic substances, especially in aqueous solutions, which sensor comprises the immobilised fluoroionophores in an active layer; b) a method for the qualitative and quantitative determination of ions, polar substances or lipophilic substances, especially in aqueous solutions, using the optical sensor, and c) a composition, as a coating composition for sensors, of a polymer having covalently bound fluoroionophores or of a polymer in which there is incorporated an inorganic or organic carrier material to the surfaces of which fluoroionophores have been covalently bound.

The optical determination of ions has recently gained greater importance, the presence or concentration of ions being measured, for example, by means of a change in the absorption or fluorescence of a suitable dye. The sensors, also called optrodes, generally consist of a transparent support material and an active layer. The active layer normally comprises a transparent hydrophobic polymer and a lipophilic plasticiser for the purpose of obtaining adequate diffusion of the ions and adequate solubility of the active components. Active components are a specific ionophore as a complexing agent for ions, a counterion for maintaining electrical neutrality, and an indicator substance which, as a result of a chemical change or a physical change in the environment, emits a measurable optical signal. The disadvantages of many such optical sensors are that their response times are too long, they are not sufficiently stable, they are pH-dependent, and the active constituents are washed out.

The response times may be shortened by covalent linkage of ionophore and fluorophore to form the so-called fluoroionophores. Such fluoroionophores are known from WO 89/00997 and U.S. Pat. No. 4,367,072.

In *J. Mater. Chem.* 4(1), (1994), pp. 145–151, Perez-Jimenez et al describe two novel fluoroionophores that comprise 4 anthracene units covalently bound to calix[4]arene via an amide or ester bond. Disadvantageous fluoroescence-quenching effects may occur as a result of the close adjacency of the four anthracene units in the molecule.

EP 0 484 865 describes an optical potassium sensor that comprises a crown ether as ionophore covalently linked to two fluorophores. In order to disperse the fluoroionophore, the polymer gel is prepared in the presence of the functional-group-free fluoroionophore, the fluorophore being non-covalently bound to the polymer gel.

EP 0 578 630 describes a sensor membrane for an optical sensor having an indicator substance that is ionically bound to the polymer matrix of the sensor membrane. The indicator substance is likewise in the form of a pair of ions and is anchored in the polymer membrane by a counterion balancing the electrical charge of the dye molecule. The counterion is derived from compounds that comprise an ionic group and a) an oligomer radical of the monomer that forms the basis of the polymer matrix in question, b) long-chained alkyl or alkylene groups or c) silyl groups. When aqueous test samples, such as, for example, blood are used, even with that method it is not possible effectively to prevent the fluoroionophore from being washed out.

A substantial disadvantage of the methods described hitherto is that the fluoroionophores are in time washed out of the active layer of a sensor. The result is that the usable life of the sensors is too short and, even where their service life is relatively long, the sensors still have to be recalibrated.

It has now, surprisingly, been found that fluoroionophores having a functional group on the fluorophore can be covalently bound to the functional groups of an inorganic or organic material and still be suitable for fluorescence detection. It is in that manner possible virtually completely to prevent the fluoroionophore from being washed out of the active layer of the sensor. The usable life of the sensor is consequently considerably increased. Undesired error corrections of the measured values (drift) caused by inaccurate measurements resulting from the fluoroionophore being washed out can be avoided practically completely.

It has also, surprisingly, been found that the selective binding affinity of the ionophore for the ions is not significantly impaired, or is not impaired at all, by the covalent bonding or by the introduction only of a functional group.

It has also, surprisingly, been found that the bonding of ions to the ionophores of the covalently bound fluorojonophores results in an adequate perturbation of the fluorescing group, the complexing of ions by way of interactions between fluorophore and ionophore leading to a measurable signal change, with the result that measurements that are substantially independent of pH are possible. Consequently, direct analysis of ions in body fluids (blood, urine, serum), natural waters or waste water is possible.

The invention accordingly relates firstly to fluoroionophores, functionalised with reactive groups, of formula (I)

wherein

I is a monovalent residue of an ionophore,

F is a divalent residue of a fluorophore,

G is a functional group and $R_1$ and $R_2$ are each independently of the other a direct bond or a bridging group.

Preferably, $R_1$ and $R_2$ are each independently of the other a bridging group.

Ionophores are natural or synthetic organic compounds that contain a plurality of mostly alternating electron-rich hetero atoms such as, for example, S, N and especially O, in an open-chained or cyclic carbon chain and that enable the ions to be measured to be selectively complexed. Such ionophores are described, for example, in US-A-4,645,744.

The monovalent ionophores from which I in formula (I) is derived may be substances that have an oligoether, polyether, oligoester, polyester, oligoamide or polyamide structure. Examples of such suitable substances may be crown ethers, coronandenes, cryptandenes, calixarenes, podandene or derivatives thereof, also cyclic peptides, for example valinomycin, nonactin, peptides such as gramicidin, and peptides which in the presence of the ion to be determined change their secondary, tertiary or quaternary structure for bonding the ion; it is also possible to use tetrahydrofuran-containing macrolides bonded via ester bridges, and analogous substances that are able to regulate transport in biological systems, or cyclic oligosaccharides, such as, for example, cyclodextrins or cyclophanes.

The functional group G may be a carboxy, sulfonic acid, acid halide, amide, thiol, amine alcohol, cyanate, isocyanate, oxime, aldehyde or ketone group or a polymerisable group.

The functional group G is preferably a hydroxyl, thiol or amine group.

The functional group G may also be a polymerisable group and in that case is preferably a vinyl group that is unsubstituted or substituted by $C_1$–$C_4$alkyl.

The polymerisable group is bonded to the fluorophore preferably via the bridging group $R_2$. The polymerisable radical may be selected from the group —O—$R_8$, —S—$R_8$, —N$R_7R_8$, —N$R_7$C(O)$R_8$, —OC(O)$R_8$, —C(O)O$R_8$, —C(O)N$R_7R_8$, —CH=N—O—$R_8$ and —NH—C(O)—N$R_7R_8$, wherein $R_7$ is H or $C_1$–$C_4$alkyl and $R_8$ is an olefinic group having from 1 to 12 carbon atoms, preferably from 1 to 4 carbon atoms, it being possible for those groups to be bonded to the fluorophore directly or via a $C_1$–$C_{20}$alkylene radical. The polymerisable radicals are preferably —N$R_7$C(O)$R_8$ wherein $R_7$ is preferably H and $R_8$ is an olefinic group.

$R_8$ is preferably an ethylenically unsaturated organic group of formula (V)

wherein $R_9$ is H or $C_1$–$C_4$alkyl, especially methyl, and $R_{10}$ is H, $C_1$–$C_{12}$alkyl, phenyl or benzyl.

$R_9$ is preferably H or methyl and $R_{10}$ is preferably H.

The polymerisable group may be derived from ethylenically unsaturated alcohols, amines or isocyanates, such as, for example, allyl alcohol, allylamine, allyl isocyanate, crotonyl alcohol; monoesters or monoamides of dicarboxylic acids and unsaturated alcohols and amines; functional styrenes, such as, for example, chloromethylstyrene, hydroxystyrene, hydroxyethoxystyrene, styreneamine, styrene-hydroxyethylamine, styrenecarboxylic acid, styrenesulfonic acid, vinylhydroxyethyl ether, acrylic acid, methacrylic acid, acrylic and methacrylic acid amide, acrylic and methacrylic acid $C_2$–$C_6$hydroxyalkyl amides, acrylic and methacrylic acid $C_2$–$C_6$hydroxyalkyl esters.

I is bonded to F directly or via a bridging group $R_1$; F is bonded to G directly or via a bridging $R_2$.

The bridging groups $R_1$ and $R_2$ may contain in the chain from 1 to 30 atoms, preferably from 1 to 20 atoms and especially from 1 to 12 atoms, selected from the group C, O, S and N. The bridging group is preferably a hydrocarbon radical that may be interrupted by one or more hetero atoms from the group O, S and N. For an adequate intramolecular interaction between fluorophore and ionophore in the same molecule it may be expedient to select short bridging groups, for example those having from 1 to 6, preferably from 1 to 4, atoms in the chain. An adequate change in the signal will, however, also occur in the case of longer bridging groups, since in that case there is intermolecular interaction between different molecules.

The bridging group $R_1$ may correspond to formula (II)

and the bridging group $R_2$ may correspond to formula (III)

wherein $X_1$, $X_2$, $X_3$ and $X_4$ are each independently of the others a direct bond or $X_1$, $X_2$, $X_3$ and $X_4$ are each independently of the others selected from the groups —O—, —S—, —N$R_5$—, —C(O)—O—, —O—C(O)—, —O—C(O)—O—, —SO$_2$—O—, —O—SO$_2$—, —O—SO$_2$—O—, —N$R_5$—C(O)—, —C(O)—N$R_5$—, —N$R_5$—C(O)—O—, —O—C(O)—N$R_5$—, —N$R_5$—C(O)—N$R_5$—, —N$R_5$SO$_2$—, —SO$_2$—N$R_5$—, —N$R_5$—SO$_2$—O—, —O—SO$_2$N$R_5$— and —N$R_5$SO$_2$—N$R_5$—, $R_5$ is H or $C_1$–$C_{30}$alkyl, $C_5$- or $C_6$-cycloalkyl, $C_5$- or C6-cycloalkyl-methyl or -ethyl, phenyl, benzyl or 1-phenyleth-2-yl, $R_3$ and $R_4$ are each independently of the other a divalent bridging group, r and s are each independently of the other 0 or 1, with the proviso that r or s is 1 when $X_1$ or $X_3$ is one of the mentioned groups.

When $R_5$ is alkyl it has preferably from 1 to 6 carbon atoms and especially from 1 to 4 carbon atoms. Examples include methyl, ethyl, n-propyl, isopropyl, butyl, hexyl and octyl. When $R_5$ is cycloalkyl it is preferably cyclohexyl, and when $R_5$ is cycloalkylmethyl it is preferably cyclohexylmethyl. In a preferred embodiment, $R_5$ is H or $C_1$–$C_4$alkyl.

The divalent bridging groups $R_3$ and $R_4$ are preferably hydrocarbon radicals that each independently of the other has preferably from 1 to 30 carbon atoms, more preferably from 1 to 18 carbon atoms, especially from 1 to 12 carbon atoms and more especially from 1 to 8 carbon atoms, and is unsubstituted or mono- or poly-substituted by $C_1$–$C_4$alkyl, $C_1$–$C_4$alkoxy or by=O. The hydrocarbon radical may also be interrupted one or more times by hetero atoms selected from the group —O—, —S— and —N$R_5$— wherein $R_5$ is preferably H or $C_1$–$C_4$alkyl.

The divalent bridging groups $R_3$ and $R_4$ each independently of the other may be, for example, $C_1$–$C_{20}$alkylene, preferably $C_2$–$C_{12}$alkylene, which may be linear or branched. Examples include methylene, ethylene, 1,2- or 1,3-propylene, 1,2-, 1,3- or 1,4-butylene, pentylene, hexylene, octylene, dodecylene, tetradecylene, hexadecylene and octadecylene.

The divalent bridging groups $R_3$ and $R_4$ may be, for example, polyoxaalkylene having from 2 to 12, especially from 2 to 6, and more especially from 2 to 4, oxaalkylene units, and from 2 to 4, preferably 2 or 3, carbon atoms in the alkylene radical. $R_3$ and $R_4$ are especially polyoxaethylene or polyoxapropylene having from 2 to 6 oxaalkylene units.

The divalent bridging groups $R_3$ and $R_4$ each independently of the other may be, for example, $C_5$–$C_{12}$-, especially $C_5$–$C_8$- and more especially $C_5$- or $C_6$-cycloalkyl, such as, for example, cyclopentylene, cyclohexylene, cyclooctylene or cyclododecylene.

The divalent bridging groups $R_3$ and $R_4$ may be, for example, $C_5$–$C_{12}$-, especially $C_5$–$C_8$- and more especially $C_5$- or $C_6$-cycloalkyl-$C_1$-$C_{12}$- or preferably —$C_1$–$C_4$-alkyl. Examples include cyclopentyl-$C_nH_{2n}$- and cyclohexyl-$C_nH_{2n}$-, wherein n is from 1 to 4. -Cyclohexyl-$CH_2$— is especially preferred.

The divalent bridging groups $R_3$ and $R_4$ each independently of the other may be, for example, $C_5$–$C_{12}$-, especially $C_5$–$C_8$- and more especially $C_5$- or $C_6$-cycloalkyl-$(C_1$–$C_{12}$alkyl$)_2$— or preferably —$(C_1$–$C_4$alkyl$)_2$. Examples include cyclopentyl-$(C_nH_{2n}$—$)_2$ and cyclohexyl-$(C_nH_{2n}$—$)_2$, wherein n is from 1 to 4. —$CH_2$-Cyclohexyl-$CH_2$— is especially preferred.

The divalent bridging groups $R_3$ and $R_4$ each independently of the other may be, for example, $C_6$–$C_{14}$arylene, especially $C_6$–$C_{10}$oarylene, for example naphthylene or especially phenylene.

The divalent bridging groups $R_3$ and $R_4$ each independently of the other may be, for example, $C_7$–$C_{20}$oaralkylene, especially $C_7$–$C_{12}$aralkylene. Arylene-$C_nH_{2n}$— wherein arylene is naphthylene or especially phenylene and n is from 1 to 4, is preferred. Examples are benzylene and phenylethylene.

The divalent bridging groups $R_3$ and $R_4$ each independently of the other may be, for example, arylene —$(C_nH_{2n}$—$)_2$— wherein arylene is preferably naphthylene or especially phenylene and n is from 1 to 4. Examples are xylylene- and phenylene —$(CH_2CH_2)_2$—.

In a preferred embodiment, the bridging group $R_2$ is a divalent radical in which $X_3$ is preferably NH, r is 1, $R_4$ is $C_2$–$C_{18}$alkylene, $X_4$ is preferably —$NR_5$—C(O)— wherein $R_5$ is H, and G is vinyl or methallyl, and $X_1$ in the bridging group $R_1$ is preferably —$NR_5$— in which $R_5$ is H, r is 0 and $X_2$ is a direct bond.

The ionophores may be, for example, $Ca^{2+}$ ionophores that are derived from the formula

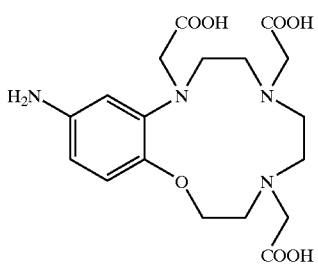

[J. Org. Chem. 1993, 58, 4681–4684], or $Ca^{2+}$ ionophores that are derived from the formula

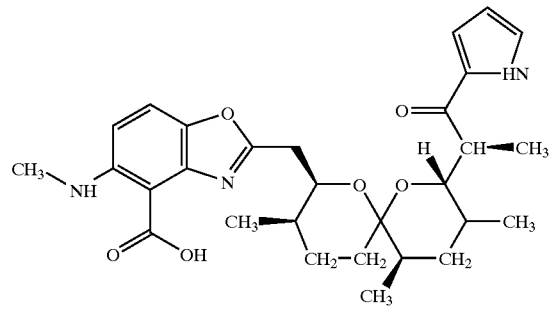

[J. Am. Chem. Soc. 1994, 116, 4505–4506], or Na+ ionophores that are derived from the formula

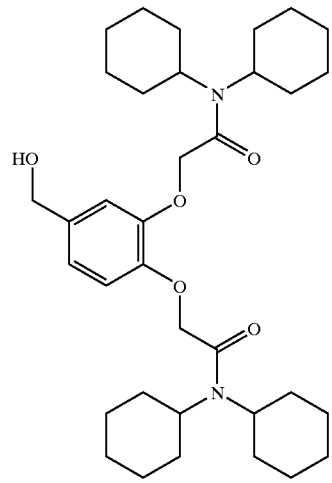

[ETH 4120-Analoges *Anal. Chim. Acta* 1990, 233, 295].

The ionophores are derived preferably from calix[4] arenes, especially from calix[4]arenes of the formula (IV)

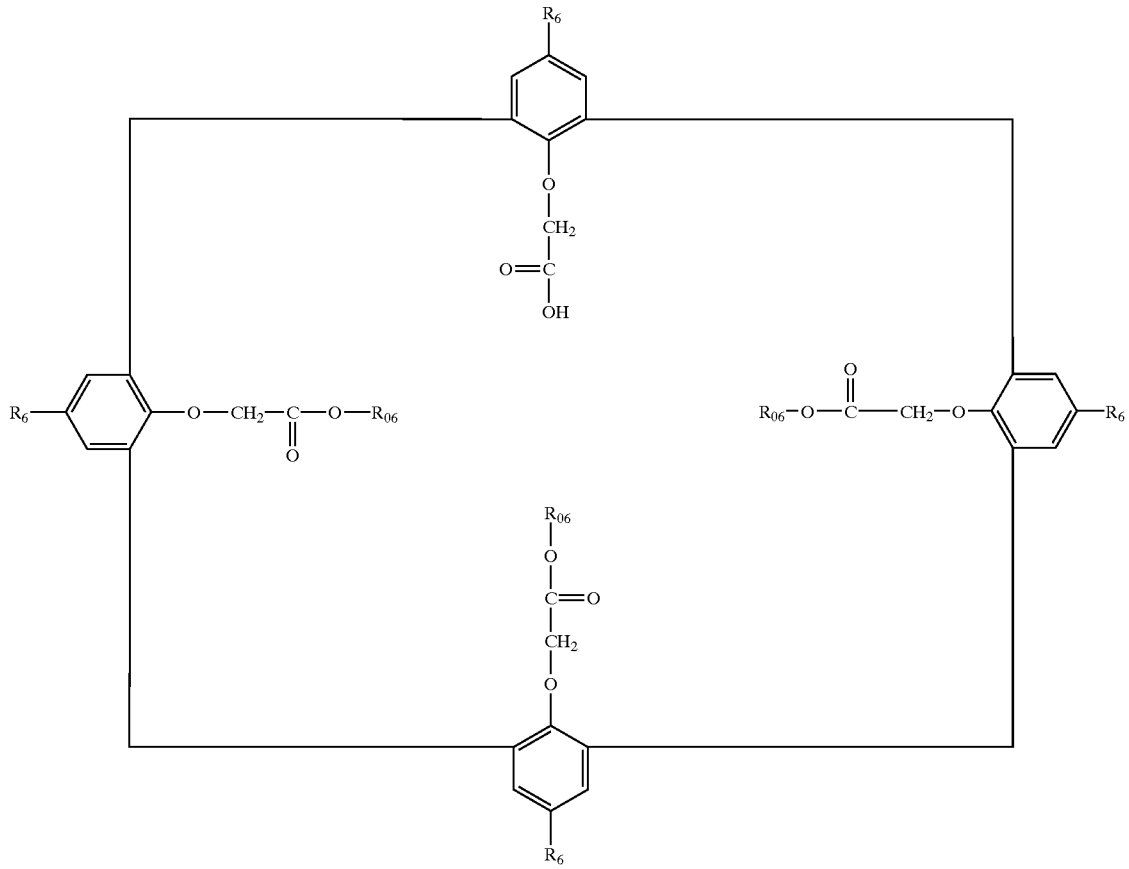

(IV)

wherein $R_{06}$ is H or substituted or unsubstituted $C_1$–$C_{20}$alkyl, and $R_6$ is H or substituted or unsubstituted $C_1$–$C_{30}$alkyl.

$R_{06}$ is especially linear or branched $C_1$–$C_{12}$alkyl, more especially linear or branched $C_1$–$C_8$alkyl.

Examples of alkyl are methyl, ethyl and the position isomers of propyl, butyl, pentyl, hexyl, heptyl, octyl nonyl and decyl.

In a preferred embodiment $R_{06}$ is H or $C_1$–$C_4$alkyl.

More especially $R_{06}$ is tertiary butyl or ethyl.

$R_6$ is especially linear or branched $C_1$–$C_{10}$alkyl more especially linear or branched $C_1$–$C_4$alkyl.

Examples of alkyl are methyl, ethyl and the position isomers of propyl, butyl, pentyl, hexyl, heptyl, octyl, nonyl and decyl.

In a preferred embodiment $R_6$ is H or $C_1$–$C_4$alkyl.

More especially $R_6$ is tertiary butyl.

The fluorophores from which F in formula (I) is derived are composed preferably of carbonyl groups, C—C double bonds and aromatic rings, more especially condensed ring systems, such as naphthaienes, anthracenes, benzofurans, benzodiazines, benzotrioxazines, benzotriazepines, pyrenes and coumarins.

The fluorophores from which F in formula (I) is derived may be fluorescein or derivatives thereof, for example fluorescein derivatives of the formulae:

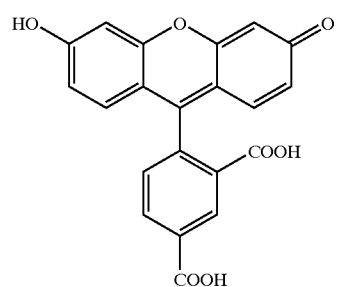

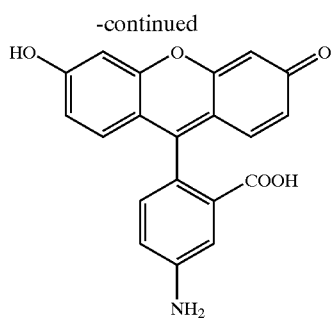
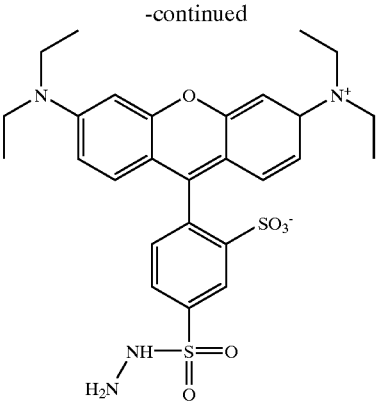
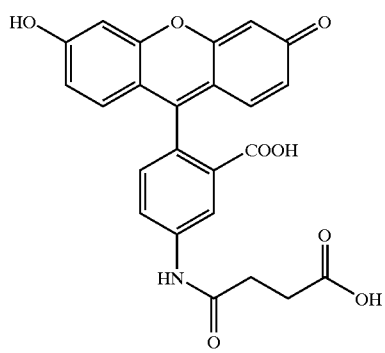
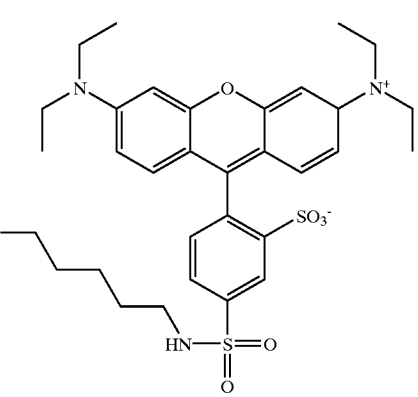
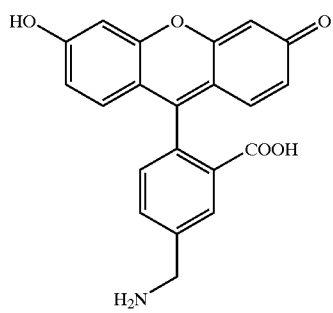
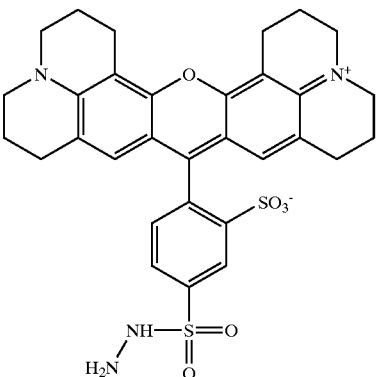
or rhodamines or derivatives thereof, for example of the formulae:
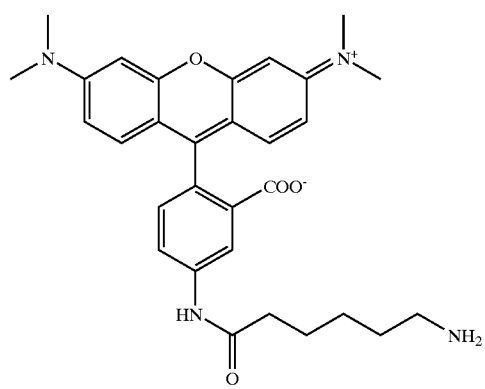
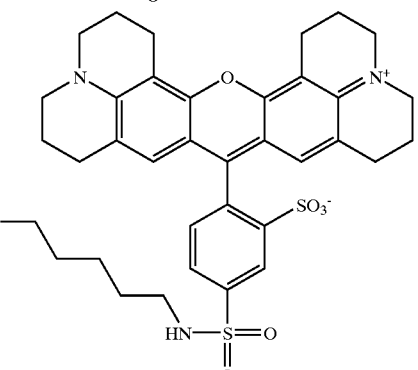
or acridines or derivatives thereof, for example of the formula

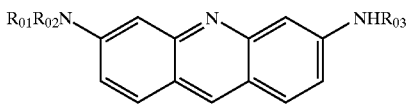

wherein $R_{01}$ and $R_{02}$ are each independently of the other H or $C_1$–$C_{20}$alkyl and $R_{03}$ is H or $C_1$–$C_6$alkyl, or carbocyanines, for example

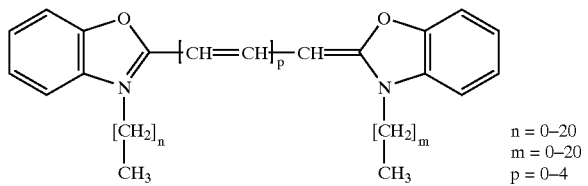

$n = 0$–$20$
$m = 0$–$20$
$p = 0$–$4$ or merocyanines, for example merocyanine 540 or derivatives thereof

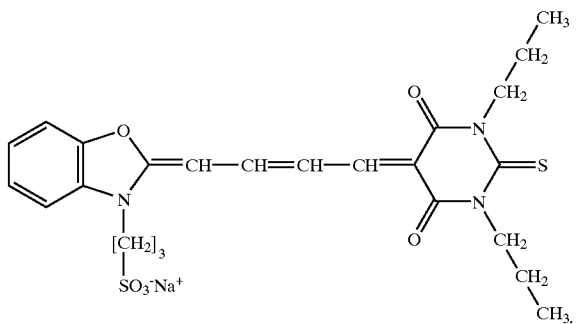

The fluorophore is derived preferably from acridine or rhodamine or derivatives thereof, especially from 3,6-diaminoacridines.

The fluoroionophores to be used according to the invention are preferably compounds of formula (Ia)

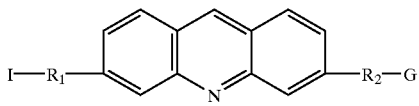

(Ia)

wherein I, $R_1$, $R_2$ and G have the meanings and preferred meanings indicated for the compound of formula (I).

More especially preferred are fluoroionophores of formula (Ia) wherein $R_2$ is a bridging group of formula (III)

(III)

wherein $X_3$ is $NR_5$ in which $R_5$ is H, $R_4$ is $C_1$–$C_{18}$alkylene, especially $C_1$–$C_8$alkylene and more especially $C_1$–$C_3$alkylene, $X_4$ is —$NR_{04}$—C(O)— in which $R_{04}$ is H or $C_1$–$C_8$alkyl, preferably H, and s is 1.

More especially preferred are fluoroionophores of formula (Ia) in which the bridging group $R_1$ corresponds to formula (II)

(II), wherein $X_1$ is as defined hereinbefore for the compound of formula (II), $X_1$ preferably being NH, $X_2$ is a direct bond and r is 0.

More especially preferred are fluoroionophores of formula (Ia) wherein 1, $R_1$ and $R_2$ have the meanings and preferred meanings given hereinbefore for the compound of formula (I) and G is a polymerisable group, especially a vinyl group, that is unsubstituted or substituted by $C_1$–$C_4$alkyl, more especially an ethylenically unsaturated organic group of formula (V)

(V)

wherein $R_9$ is H or $C_1$–$C_4$alkyl, especially methyl, and $R_{10}$ is H, $C_1$–$C_{12}$alkyl, phenyl or benzyl, especially H.

More especially preferred are fluoroionophores of formula (Ia)

wherein $R_2$ is a bridging group of formula (III)

(III)

wherein $X_3$ is $NR_5$ in which $R_5$ is H, $R_4$ is $C_1$–$C_{18}$alkylene, especially $C_1$–$C_8$alkylene and more especially $C_1$–$C_3$alkylene, $X_4$ is —$NR_{04}$—C(O)— in which $R_{04}$ is H or $C_1$–$C_8$alkyl, preferably H, and s is 1, wherein the bridging group $R_1$ corresponds to formula (II)

(II)

wherein $X_1$ is as defined hereinbefore for the compound of formula (II), $X_1$ preferably being NH, $X_2$ is a direct bond, and r is 0, and wherein G is a polymerisable group, especially a vinyl group, that is unsubstituted or substituted by $C_1$–$C_4$alkyl, more especially an ethylenically unsaturated organic group of formula (V)

(V)

wherein $R_9$ is H or $C_1$–$C_4$alkyl, especially methyl, and $R_{10}$ is H, $C_1$–$C_{12}$alkyl, phenyl or benzyl, preferably H.

More especially preferred are fluoroionophores of formula (Ia)

wherein $R_2$ is a bridging group of formula (III)

(III)

wherein $X_3$ is $NR_5$ in which $R_5$ is H, $R_4$ is $C_1$–$C_{18}$alkylene, especially $C_1$–$C_8$alkylene and more especially $C_1$–$C_3$alkylene, $X_4$ is —$NR_{04}$—C(O)— in which $R_{04}$ is H or $C_1$–$C_8$alkyl, preferably H, and s is 1, wherein the bridging group $R_1$ corresponds to formula (II)

$$—X_1—(R_3)_r—X_2— \qquad (II)$$

wherein $X_1$ is as defined hereinbefore for the compound of formula (II), $X_1$ preferably being NH, $X_2$ is a direct bond and r is 0, and wherein G is a polymerisable group, especially a vinyl group, that is unsubstituted or substituted by $C_1$–$C_4$alkyl, and more especially an ethylenically unsaturated organic group of formula (V)

$$—CR_9\!\!=\!\!CHR_{10} \qquad (V)$$

wherein $R_9$ is H or $C_1$–$C_4$alkyl, especially methyl, and $R_{10}$ is H, $C_1$–$C_{12}$alkyl, phenyl or benzyl, especially H, and wherein I is a calixarene.

There may be mentioned specifically, for example, the following fluoroionophores of the formula

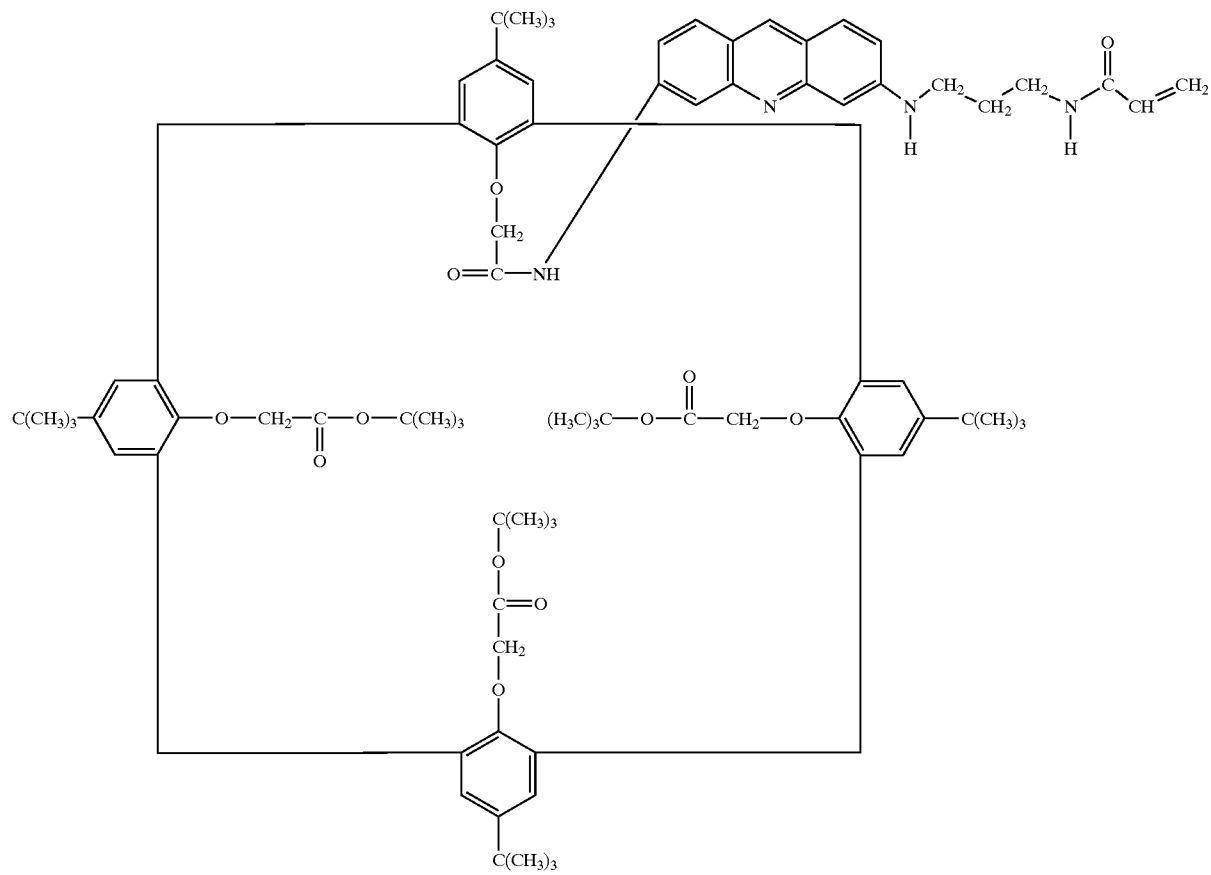

and of the formula
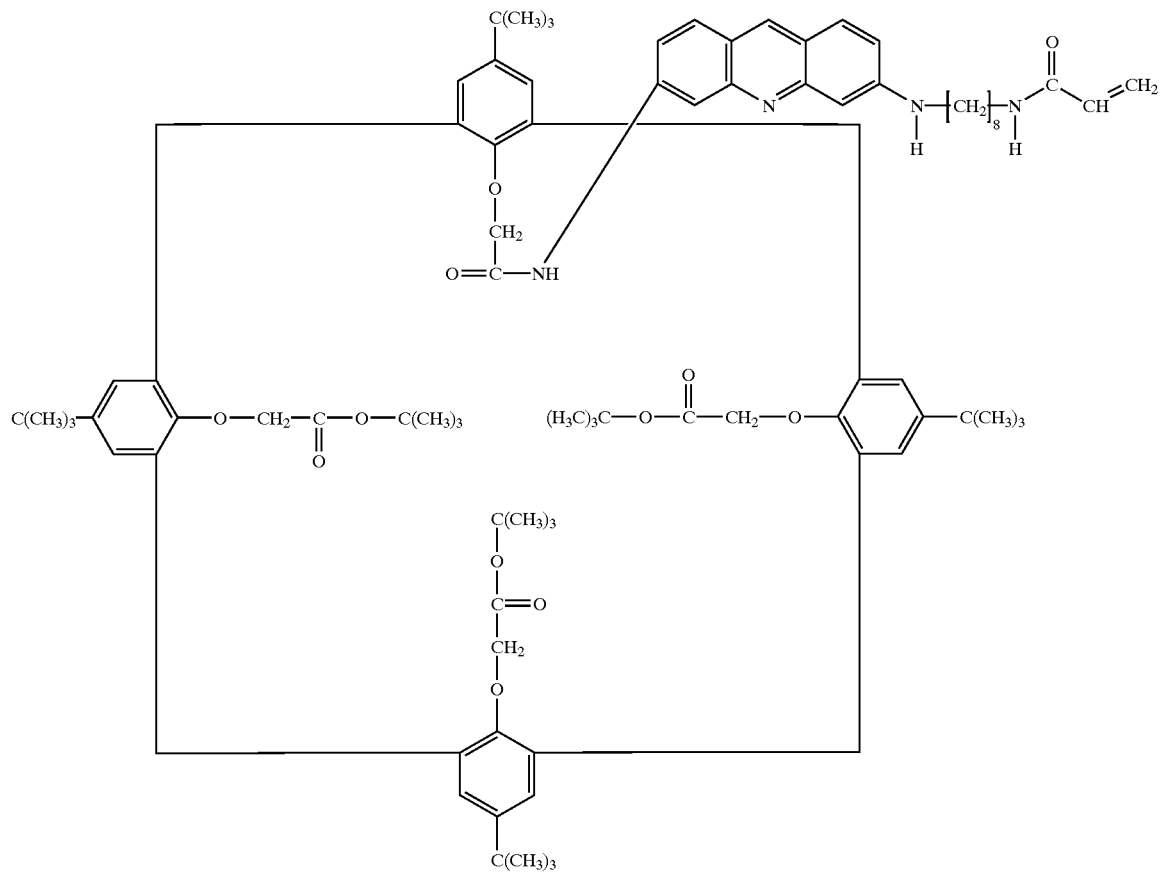

and of the formula

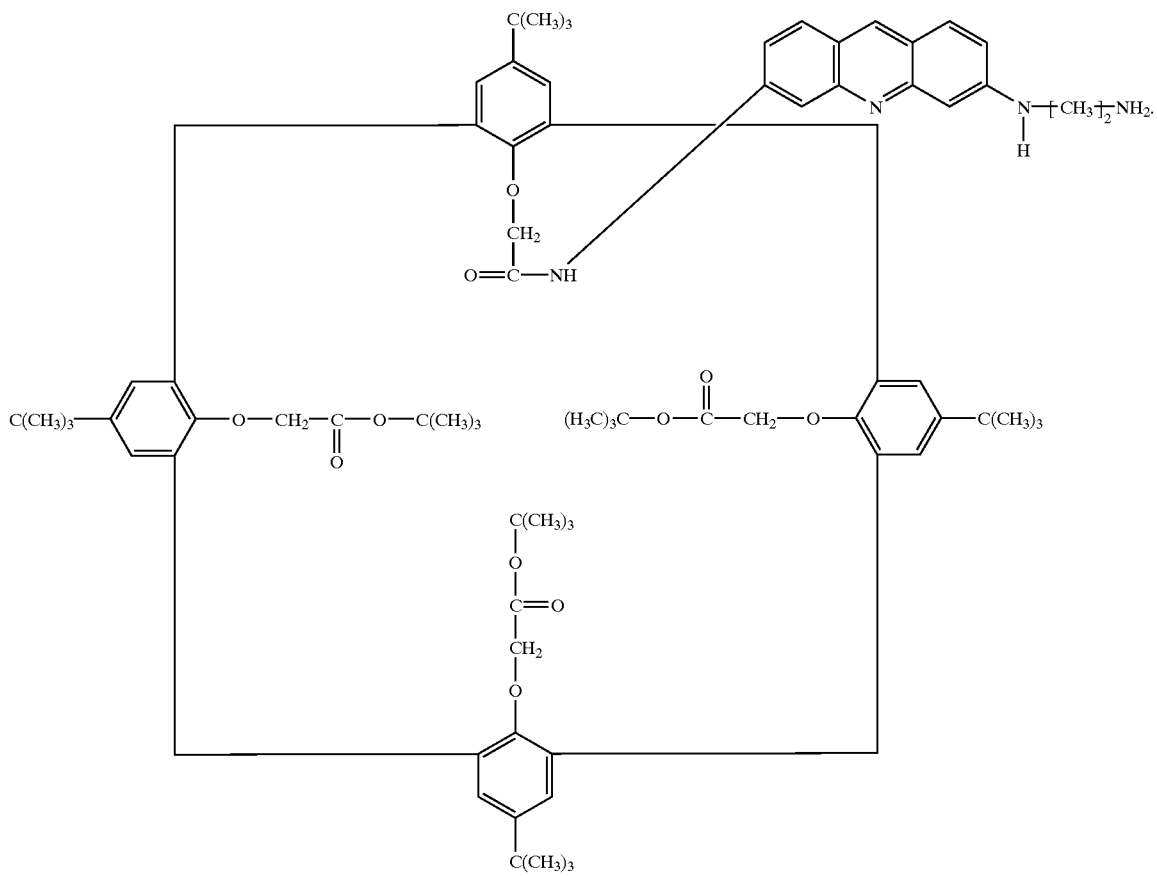

The invention relates also to a process for the preparation of a compound of formula (I) which comprises reacting an ionophore of the formula

with a fluorophore of the formula

in which formulae 1, $R_1$, F, G and $R_2$ are as defined for formula (I), and

Y and Y' are functional groups that react with one another.

In order to prepare a compound of formula (I), the functional groups of the difunctional fluorophore may first of all be asymmetrically protected by protecting groups and, as appropriate, may be activated for the purpose of linking to a functional bridging group. The chain can then be extended at that functional group and/or a polymerisable group may be bonded to that functional group by known methods. Known methods are, for example, etherification, esterification, amidation, urea formation and urethane formation.

The compounds of formulae (Ic) and (Ib) may be used in equimolar amounts.

The functional groups may be activated by activated esters.

Protecting groups and methods of derivatising functional groups are known from organic chemistry textbooks (E. Breitmaier, Günther Jung; Organische Chemie II (1983); Georg Thieme Verlag Stuttgart, New York p. 342, 409ff).

The functional groups may be protected, for example, by derivatisation. Functional groups of the —XH type (X=O, S, NH) may be protected by acylation and acyl derivatives or carbonic acid derivatives may thus be prepared. Carboxy-protecting groups are known from peptide synthesis, for example methanol or ethanol, dimethylethylene, p-toluenesulfonic acid or —$CH_2N_2$. Protecting groups for amino functions may be, for example, benzyloxycarbonyl, tert-butoxycarbonyl, p-toluenesulfonyl, 2-nitrophenylsulfenyl, trifluoroacetyl or fluorenylmethoxycarbonyl.

The linkage via functional groups may be carried out in accordance with generally known methods. It is, in principle, also possible to convert any functional groups that are present into different functional groups, for example to convert —$CH_2OH$ groups by oxidation into carboxylic acids, carboxylic acids into amides or halides, amine groups into isocyanate groups, and alcohols or amines into carbonates or urethanes. It is also possible for alcohols or amines to be reacted first of all with halocarboxylic acids (for example chloroacetic acid). Chain-extenders, for example epoxides, aziridines, diols, diamines, dicarboxylic acids or esters and diisocyanates, may also be employed one or more times in succession, thus determining the length of the bridging group in a defined manner. Those linkage methods and procedures are known and are described in the specialist literature.

The reactions may be carried out with customary inert organic solvents at temperatures of from 0° C. to 200° C.

Suitable inert solvents are, for example, protic polar solvents and aprotic solvents, which may be used alone or in the form of mixtures of at least two solvents. Examples are: water, alkanols (methanol, ethanol, propanol, butanol), ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylic acid esters and lactones (ethyl acetate, methyl propionate, ethyl benzoate, 2-methoxyethyl acetate, γ-butyrolactone, δ-valerolactone, pivalolactone), carboxylic acid amides and lactams (N,N-dimethylformamide, N,N-diethylformamide, N,N-dimethylacetamide, tetramethylurea, hexamethylphosphoric acid triamide, γ-butyrolactam, ε-caprolactam, N-methylpyrrolidone, N-acetylpyrrolidone, N-methylcaprolactam), sulfoxides (dimethyl sulfoxide)-, sulfones (dimethylsulfone, diethylsulfone, trimethylenesulfone, tetramethylenesulfone), tertiary amines (N-methylpiperidine, N-methylmorpholine), aliphatic and aromatic hydrocarbons, for example petroleum ether, pentane, hexane, cyclohexane, methylcyclohexane, benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile).

Solvents preferred from the ecological point of view are water, alkanols and mixtures of water with water-miscible solvents, using polymerisable monomers that are soluble in those solvents.

The compounds of formula (I) may be isolated in customary manner by precipitation, crystallisation, distillation or extraction and, where appropriate, may be purified by means of recrystallisation or chromatography.

Where acids may be formed in the reactions, an acid acceptor is added, for example an alkali metal carbonate or a tertiary amine, especially a sterically hindered tertiary amine.

Further details of the preparation of a compound of formula (I) will be found in the Examples.

The invention relates also to a composition comprising (a) an inorganic or organic carrier material to which (b) a fluoroionophore of formula (I) is bonded via the functional group G directly or via a bridging group.

In the case of the fluoroionophores of formula (I) that are covalently linked to the functional groups of a carrier material via their reactive group G, a distinction can be made between two embodiments, namely (A) polymers of monomers having covalently bound fluoroionophores and optionally (B) finely divided inorganic or organic carrier materials that have been subsequently modified on the surface for the covalent bonding of the fluoroionophores. Embodiment (B) offers the advantage over the polymers of embodiment (A), in the form of emulsion polymers (latices), of a lower consumption of fluoroionophores, since the latter have not been partially polymerised into the microparticles and consequently rendered inaccessible. The embodiments which follow relate to embodiment (B).

The carrier material may be an inorganic or organic support material. The carrier material may be opaque, translucent or transparent. Transparent carrier materials are preferred. Opaque or translucent carrier materials may be used, for example, in the preparation of thin layers. Suitable carrier materials are, for example, plastics, glass, ceramics, minerals, stone, metal oxides, metal nitrides, metal carbides, metals and metal alloys. The carrier materials contain functional groups for binding the fluoroionophores, which groups may, if necessary, be produced in a simple manner by plasma treatment, where necessary in a reactive gas atmosphere. Preferred carrier materials are plastics, for example polymers having functional groups, or polymers that have been surface-modified subsequently in order to introduce functional groups, for the covalent bonding of the fluoroionophores.

In the case of inorganic carrier materials, the functional groups are especially amine groups and more especially hydroxyl groups. The functional groups are generally provided with anchor groups to which the fluoroionophores are bonded directly or via a bridging group. Silanes that have a functional group are preferred for that purpose, for example tri($C_1$–$C_4$alkoxy)Si—$(CH_2)_p$—$NH_2$, tri($C_1$–$C_4$alkoxy)Si—$(CH_2)_p$—OH, tri($C_1$–$C_4$alkoxy)Si—$(CH_2)_p$—NH—$CH_2CH_2$—$NH_2$, tri($C_1$–$C_4$alkoxy)Si—$(CH_2)_p$—C(O)OH, tri($C_1$–$C_4$alkoxy)-(prop-1-en-3-yl)silane, tri$C_1$–$C_4$alkoxy)-glycidoxysilane or tri($C_1$–$C_4$alkoxy)Si—$(CH_2)_p$—NCO, wherein p is from 2 to 12, especially from 2 to 6 and more especially from 2 to 4. Examples include γ-aminopropyl-trimethoxy- or -triethoxy-silane, γ-hydroxypropyl-trimethoxy- or -triethoxy-silane and 2-trimethoxy- or 2-triethoxy-silylpropionic acid.

In the case of organic carrier materials, the functional groups are preferably amine, hydroxyl, carboxy, -$SO_3H$ or isocyanate groups. They may be polymers that have been modified subsequently (for example by means of plasma treatment) or milled natural or synthetic polymers having functional groups. Suitable synthetic polymers include emulsion polymers and latices of at least one monomer having functional groups. Examples of natural polymers are polysaccharides, such as cellulose, starch, carageenan and chitosan, which may have been partially etherified by $C_1$–$C_4$alkyl or partially acylated by $C_1$–$C_8$acyl. Synthetic polymers having functional groups are known in large numbers or they may be prepared according to analogous processes. Examples of synthetic polymers include polyvinyl alcohol and copolymers having unsubstituted or substituted olefins as comonomers; polymethacrylic acid, polyacrylic acid and polymaleic acid and copolymers having unsubstituted or substituted olefins as comonomers; polyhydroxyalkyl acrylates, polyhydroxyalkyl methacrylates and polymaleic acid hydroxyalkyl esters and copolymers having unsubstituted or substituted olefins as comonomers; polyacrylamides and polymethacrylamides and copolymers having unsubstituted or substituted olefins as comonomers; polyaminoalkyl-acrylic acid esters, -methacrylic acid esters and -maleic acid esters and copolymers having unsubstituted or substituted olefins as comonomers; polyhydroxyalkyl or polyaminoalkyl vinyl alcohol and copolymers having unsubstituted or substituted olefins as comonomers; hydroxylated polybutadienes of butadiene, isoprene or chloroprene and copolymers having unsubstituted or substituted olefins as comonomers; hydroxy- or amino-polystyrene, chloromethylpolystyrene and polystyrenesulfonic acid and copolymers having unsubstituted or substituted olefins as comonomers; polyglycidyl ethers and hydroxyalkylated or aminoalkylated polyglycidyl ethers; and polyesters, polyamides and polyurethanes having hydroxyl-group-containing monomers. Duroplasts are also suitable, for example epoxy resins, melamine-formaldehyde resins and phenol-formaldehyde resins. Suitable comonomers are, for example, olefins, such as ethene, propene, butene, pentene, octene; vinyl chloride, vinylidene chloride; styrene; and acrylonitrile. Also suitable are crosslinked polymers, for example polymerisates having olefinic and diolefinic monomers, such as butadiene, divinylbenzene or diol-diacrylic or -methacrylic acid esters. Other suitable vinyl polymers are polyvinylpyrrolidone, polyvinylimidazole and polyvinylpyridine and copolymers having unsubstituted or substituted olefins as comonomers.

The amount of fluoroionophore covalently bound to the carrier material may be, for example, from 0.0001 to 99, preferably from 0.001 to 80, more preferably from 0.001 to 50, especially from 0.1 to 20, and more especially from 1 to 10, % by weight based on the carrier material.

In a preferred embodiment, there are ionically or covalently bound to the carrier material, in addition, radically or cationically photopolymerisable organic radicals that preferably correspond to the polymerisable organic compounds used for the preparation of a sensor membrane. Accordingly, in radically polymerisable ethylenically unsaturated systems ethylenically unsaturated compounds having functional groups are advantageously used, and in cationically polymerisable systems, such as, for example, di- or poly-epoxides, di- or poly-epoxides having functional groups are expediently used.

Ethylenically unsaturated organic compounds having functional groups and that are known in large numbers are preferred. The radicals of ethylenically unsaturated organic compounds covalently bound to the carrier material may correspond, for example, to formula VI

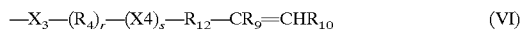  (VI)

wherein $X_3$, $X_4$ $R_4$, r and s each independently of the others has the meanings and preferred meanings indicated hereinbefore for formula III, $R_{12}$ is a direct bond, $C_1$–$C_{18}$alkylene, $C_5$- or $C_6$-cycloalkylene, $C_6$–$C_{10}$arylene or $C_7$–$C_{12}$aralkylene, $R_9$ is H or $C_1$–$C_4$alkyl, especially methyl, and $R_{10}$ is H, $C_1$–$C_{12}$alkyl, phenyl or benzyl.

$R_{12}$ as alkylene contains especially from 1 to 12 and more especially from 1 to 6 carbon atoms. Especially preferred examples are methylene, ethylene, 1,2- and 1,3-propylene and 1,2-, 1,3- and 1,4-butylene. $R_{12}$ as arylene is preferably phenylene and as aralkylene is preferably benzylene.

$R_9$ is preferably H or methyl, and $R_{10}$ is preferably H.

Ethylenically unsaturated compounds containing functional groups are, for example, ethylenically unsaturated alcohols, amines and isocyanates, such as, for example, allyl alcohol, allylamine, allyl isocyanate, crotonyl alcohol; monoesters or monoamides of dicarboxylic acids and of unsaturated alcohols and amines; functional styrenes, for example chloromethylstyrene, hydroxystyrene, hydroxyethoxystyrene, styreneamine, styrenehydroxyethylamine, styrenecarboxylic acid, styrenesulfonic acid, vinyl hydroxyethyl ether, acrylic acid, methacrylic acid, acrylic and methacrylic acid amide, acrylic and methacrylic acid $C_2$–$C_6$hydroxyalkyl amides, acrylic and methacrylic acid $C_2$–$C_6$hydroxyalkyl esters.

The amount of ionically or covalently bound radically or cationically photopolymerisable organic compounds may be, for example, from 0.001 to 99, preferably from 0.01 to 80, more preferably from 0.01 to 50, especially from 0.01 to 20, and more especially from 0.1 to 20, % by weight based on the carrier material.

The percentages by weight always add up to 100%.

The immobilisation may be carried out according to generally known processes. "Immobilisation" denotes a covalent bonding, during which it is in principle also possible to convert any functional groups that are present into different functional groups, for example to convert —$CH_2OH$ groups by oxidation into carboxylic acids, carboxylic acids into amides or halides, amine groups into isocyanate groups, alcohols or amines into carbonates or urethanes. It is also possible for alcohols or amines to be reacted first of all with halocarboxylic acids (for example chloroacetic acid). Chain extenders, for example epoxides, aziridines, diols, diamines, dicarboxylic acids or esters and diisocyanates, may also be employed one or more times in succession, thus determining the length of the bridging group in a defined manner. Those immobilisation methods and procedures are known and are described in the specialist literature. The bridging group may be built on starting from the carrier material or from the functional compound. The subsequent reaction with the functional compound or carrier material, as the case may be, results in the immobilised fluoroionophores according to the invention. The reactions may be carried out with customary inert organic solvents and at temperatures from 0° C. to 200° C.

"Finely divided" denotes that the particles have a preferably small mean diameter; the diameter of the particles may be from 5 nm to 100 μm, preferably from 10 nm to 50 μm, especially from 10 nm to 20 μm, and more especially from 20 nm to 100 nm.

The following comments relate to embodiment (A):

In another preferred embodiment of the invention the immobilised fluoroionophore is a polymer to the backbone of which monovalent residues of identical or different fluoroionophores are covalently bound directly or via a bridging group. Those polymers may be in the form of heterogeneous particles that are incorporated in a sensor membrane during its manufacture but they may alternatively, and preferably, be soluble polymers from which sensor membranes can be produced directly. The polymer may furthermore be crosslinked and form a layer or membrane.

The polymers may have monomer units comprising monovalent residues of a fluoroionophore and, if desired, comonomer units. The fluoroionophore may be bonded to the monomer directly or via a bridging group and, additionally, spacer groups The bridging groups are derived from functional groups bonded to the monomer (or to the polymer, as the case may be).

In the case of polymers the functional groups are preferably amine, hydroxyl, carboxy, —SO$_3$H or isocyanate groups. The polymers may be milled natural or synthetic polymers having functional groups. Suitable synthetic polymers include emulsion polymers and latices of at least one monomer having functional groups. Examples of natural polymers are polysaccharides, such as cellulose, starch, carrageenan or chitosan, which may have been partially etherified by C$_1$–C$_4$alkyl or partially acylated by C$_1$–C$_8$acyl. Synthetic polymers having functional groups are known in large numbers or they may be prepared according to analogous processes. Examples of synthetic polymers include polyvinyl alcohol and copolymers having unsubstituted or substituted olefins as comonomers; polymethacrylic acid, polyacrylic acid and polymaleic acid and copolymers having unsubstituted or substituted olefins as comonomers; polyhydroxyalkyl acrylates, polyhydroxyalkyl methacrylates and polymaleic acid hydroxyalkyl esters and copolymers having unsubstituted or substituted olefins as comonomers; polyacrylamides and polymethacrylamides and copolymers having unsubstituted or substituted olefins as comonomers; polyaminoalkyl-acrylic acid esters, -methacrylic acid esters and -maleic acid esters and copolymers having unsubstituted or substituted olefins as comonomers; polyhydroxyalkyl or polyaminoalkyl vinyl alcohol and copolymers having unsubstituted or substituted olefins as comonomers; hydroxylated polybutadienes of butadiene, isoprene or chloroprene and copolymers having unsubstituted or substituted olefins as comonomers; hydroxy- or amino-polystyrene, chloromethylpolystyrene and polystyrenesulfonic acid and copolymers having unsubstituted or substituted olefins as comonomers; polyglycidyl ethers and hydroxyalkylated or aminoalkylated polyglycidyl ethers; and polyesters, polyamides and polyurethanes having hydroxyl-group-containing monomers. Other suitable polymers are polyvinylpyridine, polyvinylimidazole and polyvinylpyrrolidone and copolymers having unsubstituted or substituted olefins as comonomers.

Polymers based on functionally substituted ethylenically unsaturated monomers are preferred.

In a preferred embodiment, the polymers according to the invention contain from 100 to 0.001 mol % of identical or different structural units of formula VII

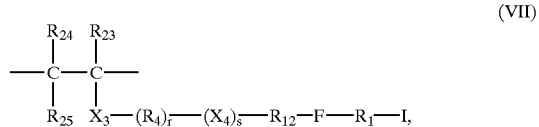

(VII)

and from 0 to 99.9 mol % of identical or different structural units of formula VIII

(VIII)

in which formulae $X_3$, $X_4$, $R_4$, $R_{12}$, r and s each independently of the others has the meanings and preferred meanings indicated hereinbefore for formula VI, I—R$_1$—F— is the residue, described in formula (I), of a fluoroionophore, $R_{23}$ and $R_{24}$ are each independently of the other H, C$_1$–C$_6$alkyl, C$_6$–C$_{10}$aryl or C$_7$–C$_{12}$aralkyl, $R_{25}$ is H or the group —C(O)O—R$_{30}$, $R_{26}$ is H, C$_1$–C$_6$alkyl, C$_6$–C$_{10}$aryl or C$_7$–C$_{12}$aralkyl, $R_{27}$ is H, F, Cl, CN, C$_1$–C$_6$alkyl or C$_6$–C$_{10}$aryl, $R_{28}$ is H, C$_1$–C$_6$alkyl or —C(O)O—R$_{29}$, $R_{29}$ is H, C$_1$–C$_6$alkyl, C$_6$C$_{10}$aryl, C$_7$–C$_{12}$aralkyl, imidazolyl, pyrrolidonyl, F, Cl, CN or the group $X_1$—(R$_1$)$_r$—(X$_2$)$_s$—H, and $R_{30}$ is H, K, Na, C$_1$–C$_{18}$alkyl, C$_1$–C$_{16}$hydroxyalkyl, cyclohexyl, cyclopentyl, cyclohexylmethyl, phenyl, C$_1$–C$_4$alkylphenyl, benzyl or C$_1$–C$_4$alkylphenylbenzyl.

$R_{23}$ and $R_{24}$ as alkyl are preferably C$_1$-C$_4$alkyl, for example methyl, ethyl, n- or iso-propyl or n-, iso- or tert-butyl, as aryl are preferably naphthyl or phenyl and as aralkyl are preferably benzyl. More especially $R_{23}$ is H and $R_{24}$ is H or methyl.

$R_{25}$ is preferably H, —C(O)OH or —C(O)O—C$_1$–C$_4$alkyl.

$R_{26}$ as alkyl is preferably C$_1$–C$_4$alkyl, for example methyl, ethyl, n- or iso-propyl or n-, iso- or tert-butyl, as aryl is preferably naphthyl or phenyl and as aralkyl is preferably benzyl. More especially $R_{26}$ is H.

$R_{27}$ as alkyl is preferably C$_1$–C$_4$alkyl, for example methyl, ethyl, n- or iso-propyl or n-, iso- or tert-butyl, and as aryl is preferably phenyl or naphthyl. More especially $R_{27}$ is H, Cl, CN, phenyl or C$_1$–C$_4$alkyl.

$R_{28}$ as alkyl is preferably C$_1$–C$_4$alkyl, for example methyl, ethyl, n- or iso-propyl or n-, iso- or tert-butyl. $R_{30}$ in the group —C(O)O—R$_{30}$ is especially H or C$_1$–C$_{12}$alkyl, more especially C$_1$–C$_6$alkyl, such as, for example, methyl, ethyl, propyl, butyl, pentyl, hexyl, heptyl, octyl, nonyl, decyl, undecyl, dodecyl, tetradecyl, hexadecyl or octadecyl. More especially $R_{28}$ is H, —C(O)OH or —C(O)—O—C$_1$–C$_4$alkyl.

$R_{29}$ as alkyl is preferably C$_1$-C$_4$alkyl, for example methyl, ethyl, n- or iso-propyl or n-, iso- or tert-butyl, as aryl is preferably phenyl or naphthyl and as aralkyl is preferably benzyl. $R_{29}$ is preferably H, C$_1$–C$_4$alkyl, phenyl, pyrrolidonyl, F, Cl, CN or the group X$_3$(R$_4$)$_r$(X$_4$)$_s$—H.

$R_{29}$ may be, for example, H, K, Na, C$_1$–C$_6$alkyl, C$_1$–C$_6$hydroxyalkyl, cyclohexyl, cyclopentyl, cyclohexylmethyl, phenyl, methylphenyl, benzyl or methyiphenylbenzyl.

The structural units of formula VII may be present in an amount of from 0.001 to 100 mol %, especially from 0.5 to 90 mol %, more especially from 0.5 to 80 mol %, more especially from 1 to 80 mol %, more especially from 1 to 60 mol %, more especially from 1 to 50 mol %, and most especially from 1 to 30 mol %.

The structural units of formula VIII may be present in an amount of from 99.9 to 0 mol %, especially from 99.5 to 0 mol %, more especially from 99.5 to 20 mol %, more especially from 99 to 20 mol %, more especially from 99 to 40 mol %, more especially from 99 to 50 mol %, and most especially from 99 to 30 mol %.

The polymers may also contain structural units having pendant unsaturated groups that are used for the crosslinking in the membrane formation.

Structural units of ethylenically unsaturated organic compounds having covalently bound olefin groups, which are known in large numbers, are preferred. The residues, covalently bound to the polymer, of ethylenically unsaturated organic compounds may correspond, for example, to structural units of formula X

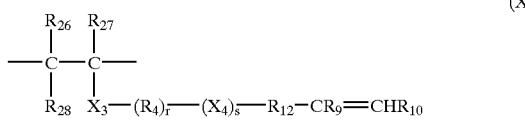

(X)

wherein
- $X_3$, $X_4$, $R_4$, $R_{12}$, r and s each independently of the other has the meanings and preferred meanings indicated hereinbefore for formula VI,
- $R_9$ is H or $C_1$–$C_4$alkyl, especially methyl;
- $R_{10}$ is H, $C_1$–$C_{12}$alkyl, phenyl or benzyl; and
- $R_{26}$, $R_{27}$ and $R_{28}$ are as defined for formula VIII.

$R_{12}$ as alkylene contains especially from 1 to 12 and more especially from 1 to 6 carbon atoms. Especially preferred examples are methylene, ethylene, 1,2- and 1,3-propylene and 1,2-, 1,3- and 1,4-butylene. $R_3$ as arylene is preferably phenylene and as aralkylene is benzylene.

$R_9$ is preferably H or methyl, and $R_{10}$ is preferably H.

The structural units of formula X may replace from 0.1 to 99.9999 mol %, especially from 0.5 to 90 mol %, more especially from 0.5 to 80 mol %, more especially from 1 to 80 mol %, more especially from 1 to 60 mol %, more especially from 1 to 50 mol %, and most especially from 1 to 30 mol % of the structural units of formula VIII.

Further, the polymers according to the invention may be crosslinked with at least difunctional monomers, for example with from 0.01 to 30 mol %, preferably from 0.1 to 15 mol %, of such monomers based on the polymer. Depending on the nature of the polymer, there may be used for that purpose at least trifunctional carboxylic acid, isocyanates, alcohols, amines or epoxides and, in the case of polymerisates, organic compounds containing at least two ethylenically unsaturated groups. Such crosslinking agents are known in large numbers. Ethylenically unsaturated crosslinking agents may be, for example, divinylbenzene, bis-dimethylmaleimide-alkylene (for example bis(dimethylmaleimidyl)-methylene or -ethylene), acrylic acid or methacrylic acid esters or amides of polyols, preferably diols to tetrols, or of polyamines, preferably diamines to tetramines. Aliphatic, cycloaliphatic and cycloaliphatic-aliphatic diols and diamines having especially from 2 to 12, more especially from 2 to 8, carbon atoms are preferred. Examples of such diols include alkylenediols, such as ethylene glycol, 1,2- and 1,3-propanediol, 1,2-, 1,3- and 1,4-butanediol, pentanediol, hexanediol, octanediol, decanediol, dodecanediol, cyclohexanediol, di(hydroxymethyl)-cyclohexane, polyoxaalkylene glycols of alkylenediols, preferably $C_2$–$C_6$alkylenediols, having especially from 2 to 100 alkylenediol units, more especially from 2 to 50 alkylenediol units and most especially from 2 to 20 alkylenediol units, such as, for example, polyethylene glycols, polypropylene glycols, polybutylene glycols and polyethylene/polypropylene glycols, also 1,1,1-trihydroxymethyl-ethane or -propane, pentaerythritol and dipentaerythritol. Examples of polyamines include ethylenediamine, 1,2- and 1,3-propanediamine, 1,2-, 1,3- and 1,4-butanediamine, 1,6-hexanediamine, diethylenetriamine, triethylenetetramine, cyclohexanediamine, amino-methylcyclohexanamine, isophoronediamine and di(aminomethyl)cyclohexane.

In a preferred embodiment the polymers according to the invention comprise at least one structural unit of formula XI

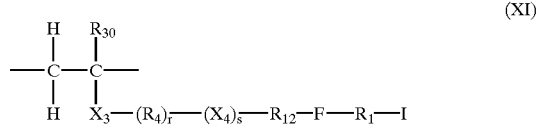

(XI)

wherein $R_{30}$ is H or methyl, and $X_3$, $X_4$, $R_4$, $R_{12}$, —F—$R_1$—I, r and s have the meanings indicated hereinbefore, including the preferred meanings and special embodiments indicated hereinbefore.

The group —$X_3$—$(R_4)_r$—$(X_4)_s$—$R_{12}$- in the structural units of formula XI is preferably —C(O)—O—, —C(O)—O—$C_1$–$C_6$alkylene-O-, —C(O)—O—($C_2$–$C_6$alkylene-O)$_u$- wherein u is from 2 to 10, —C(O)—O—($C_2$–$C_6$alkylene-O)$_u$-$C_1$–$C_6$alkylene- wherein u is from 2 to 10, and —C(O)—O—$C_1$–$C_6$alkylene-S-.

The preferred polymeric materials may comprise, in addition to the structural units of formula XI, also identical or different structural units of formula XII

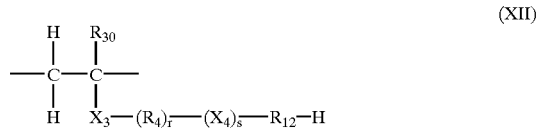

(XII)

wherein $R_{30}$, $X_3$, $X_4$, $R_4$, $R_{12}$, r and s are as defined hereinbefore. Those structural units are present especially when the compound of formula (I) is reacted with a polymer having functional groups.

The preferred polymeric materials may comprise, in addition to the structural units of formula XI, also identical or different structural units of formula XIII

(XIII)

wherein
- $R_{30}$ is H or methyl, and
- $R_{38}$ is H, $C_1$–$C_4$alkyl, $C_1$–$C_4$alkoxy, —CN, Cl, phenyl, pyrrolidonyl, pyridinyl, imidazolyl, —(O)O$R_{39}$ or —C(O)—N$R_{40}R_{41}$,
- $R_{39}$ is H or $C_1$–$C_{18}$- or preferably $C_1$–$C_{12}$-alkyl, and
- $R_{40}$ and $R_4$, are each independently of the other H or $C_1$–$C_{12}$- or preferably $C_1$–$C_6$-alkyl.

In a further preferred embodiment, the polymeric materials according to the invention having structural units of formula Xi and, where applicable, of formula XII and XIII, are crosslinked with identical or different structural units of the formula XIV or XV

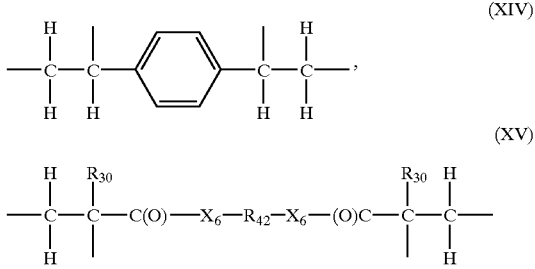

(XIV)

(XV)

wherein
- $R_{30}$ is H or methyl,
- $X_6$ is —O— or —NH— or —N($C_1$–$C_4$alkyl)-, and
- $R_{42}$ is $C_2$–$C_{12}$- or preferably $C_1$–$C_6$alkylene, cyclohexylene, cyclohexylenedimethylene, or
- $X_6$ is —O- and $R_{42}$ is $C_2$–$C_6$alkylene-($C_2$–$C_6$alkylene-O)$_2$ to $_{20}$-$C_2$–$C_6$alkylene.

In a further preferred embodiment, the polymeric materials according to the invention having structural units of formula XI and, if desired, of formulae XII, XIII, XIV and XV comprise identical or different structural units that comprise ionic groups, such as, for example—C(O)O$^-$ or —SO$_3^-$ or ammonium groups, bonded in side chains or that comprise at least two ion-forming structural units, for example structural units having amino groups and structural units having —C(O)O$^-$ or —SO$_3^-$ bonded in side chains. Those polymers are preferably emulsion polymers or a latex.

The polymers having the structural units of formula X contain those structural units preferably in an amount of from 0.1 to 30, preferably from 2 to 15, % by weight based on the polymer.

The structural units of formula XII may be present in an amount of from 99 to 0% by weight, preferably from 98 to 0% by weight. The structural units of formula XIII may be present in an amount of from 99.9 to 0% by weight, preferably from 98 to 0% by weight. The structural units of formulae XIV and XV may be present in an amount of from 0.1 to 30% by weight, preferably from 1 to 15% by weight.

The polymers according to the invention having structural units of formula VII or XI are preferably emulsion polymers.

The polymers of the invention may be prepared according to procedures known in polymer chemistry. The monomers are known or may be prepared according to known procedures. Known polymerisation processes are solution polymerisation, bulk polymerisation, emulsion polymerisation and interfacial polymerisation. Advantageously, emulsion polymerisation at high stirring speeds is used, since the immobilised fluoroionophores of the invention can be produced in the form of microparticles and subsequent treatments, such as, for example, milling, can be avoided. The milling of polymers for the preparation of microparticles is also generally known, with ball milling, for example, being suitable. In order to treat the polymers gently, the milling can be carried out with cooling. The preparation of the microparticles may also be carried out in solution, as described hereinbefore for the modification of surfaces in a heterogeneous reaction, by the reaction of natural or synthetic polymers having functional groups and functionalised fluoroionophores and, if desired, other functionalised compounds, for example functional polymerisable compounds. Microparticles can then be obtained by precipitation from the solutions or by milling the isolated modified polymers. In that preparation process the known methods for introducing spacer groups (spacers) may also be used. It is especially also possible for polymers having structural units of formula VII and other structural units having functional groups subsequently to be modified at the surface and, in addition, for polymerisable groups to be bonded covalently only to the surface of the microparticles.

The fluoroionophores according to the invention are excellently suitable as active components in optical ion sensors for the detection of ions by means of a change in fluorescence.

The invention relates also to compositions comprising a polymer of embodiment A having a covalently bound fluoroionophore, in admixture with a polymer Z.

The invention relates also to a composition comprising a polymer Z in which a finely divided inorganic or organic carrier material of embodiment B has been incorporated.

Those compositions and the polymers of embodiment A, where appropriate in dissolved form, are excellent coating compositions for the manufacture of sensors.

The amount of covalently bound fluoroionophores, polymers or carrier materials may be, for example, from 0.1 to 80, preferably from 0.1 to 50, especially from 1 to 20, more especially from 1 to 10, % by weight based on the composition.

The polymer Z may be a natural or synthetic polymer. Examples of natural polymers are polysaccharides, such as cellulose, starch, carrageenan or chitosan, which may have been partially etherified by $C_1$–$C_4$alkyl or partially acylated by $C_1$–$C_8$acyl. Synthetic polymers are known in large numbers or they may be prepared according to analogous processes. Examples of synthetic polymers include polyvinyl alcohol and copolymers having unsubstituted or substituted olefins as comonomers; polymethacrylic acid, polyacrylic acid and polymaleic acid and copolymers having unsubstituted or substituted olefins as comonomers; polyhydroxyalkyl acrylates, polyhydroxyalkyl methacrylates and polymaleic acid hydroxyalkyl esters and copolymers having unsubstituted or substituted olefins as comonomers; polyacrylamides and polymethacrylamides and copolymers having unsubstituted or substituted olefins as comonomers; polyaminoalkyl-acrylic acid esters, methacrylic acid esters and -maleic acid esters and copolymers having unsubstituted or substituted olefins as comonomers; polyhydroxyalkyl or polyaminoalkyl vinyl alcohol and copolymers having unsubstituted or substituted olefins as comonomers; hydroxylated polybutadienes of butadiene, isoprene or chloroprene and copolymers having unsubstituted or substituted olefins as comonomers; hydroxy- or amino-polystyrene, chloromethylpolystyrene and polystyrenesulfonic acid and copolymers having unsubstituted or substituted olefins as comonomers; polyglycidyl ethers and hydroxyalkylated or aminoalkylated polyglycidyl ethers; and polyesters, polyamides and polyurethanes having hydroxyl-group-containing monomers. Duroplasts are also suitable, for example epoxy resins, melamine-formaldehyde resins and phenol-formaldehyde resins. Suitable comonomers are, for example, olefins, such as ethene, propene, butene, pentene, octene; vinyl chloride, vinylidene chloride; styrene; and acrylonitrile. Also suitable are crosslinked polymers, for example polymerisates having olefinic and diolefinic monomers, such as butadiene, divinylbenzene or dioldiacrylic or -methacrylic acid esters. Other suitable vinyl polymers are polyvinylpyrrolidone, polyvinylimidazole and polyvinylpyridine and copolymers having unsubstituted or substituted olefins as comonomers.

The compositions may be applied to suitable support materials directly or in dissolved form.

The invention relates also to a material comprising (a) a support and (b) an active layer on at least one surface, wherein the active layer comprises a polymer according to the invention or a polymer in which particles of the polymer or carrier material according to the invention have been incorporated.

The support is preferably transparent and may be formed, for example, from a plastics material, such as, for example, polycarbonate or acrylic glass, mineral materials, metal oxides or glass, and may be of any shape, for example in the form of plates, cylinders, tubes, strips or fibres. Glasses are preferred.

The thickness of the layer on the support may be, for example, from 0.01 to 100 $\mu$m, preferably from 0.1 to 50 $\mu$m, especially from 0.1 to 30 $\mu$m and more especially from 0.1 to 10 $\mu$m.

Such layers may be prepared in a manner known per se, for example by dissolving the composition and, if desired, a homo- and/or co-polymer in a solvent, then casting to form a s film and subsequently removing the solvent. After removal of the solvent the film can be released from the substrate and a free-standing membrane is obtained.

Other processes that may be used for the production of the membrane are those known from surface-coating technology, for example spin-coating, spraying or knife application processes. Spin-casting processes are preferred. The material according to the invention may also be obtained by injection-moulding or extrusion processes. Suitable solvents include water, alcohols, ethers, esters, acid amides and ketones. Readily volatile solvents, especially tetrahydrofuran, or solvent mixtures, are especially suitable.

The membrane may be transparent or slightly opaque. It is preferably transparent. The layer is preferably hydrophilic.

The optical range in which the material as sensor can be excited extends from the ultraviolet range to the infrared range. The immobilised fluorophore-ionophores to be used in accordance with the invention have very suitable absorption and emission wavelength ranges that allow the use of known economically priced low-energy light sources, for example halogen or xenon lamps or light-emitting diodes. The preferred excitation source is a light-emitting diode having a wavelength of approximately 400 nm and above. The detectors used to detect the fluorescence may be, for example, photodiodes. Commercially obtainable optical fibres may be used in the excitation and detection. The sensor may therefore be changed after use on a patient.

The optical sensor is suitable especially for the quantitative determination of ions, especially cations, more especially metal cations, that are present in blood plasma, for example calcium, sodium or potassium cations, in an aqueous environment preferably using fluorescence spectrometry, measurements advantageously being taken in the region of the emission maxima. The determinations may be effected within short periods of time with a high degree of accuracy even in the case of low concentrations (for example extending from the molar range to the nanomolar range).

A very important advantage of the immobilised fluoroionophores is that they offer the possibility of carrying out measurements that are substantially independent of pH value. There is a much freer choice of fluoroionophores since proton exchange at the fluorophore is not necessary for the detection of ions. In addition, direct measurement of the solution to be analysed is possible, which is of considerable commercial advantage. If desired, however, it is also possible in some cases for the measurements to be carried out in buffered analysis solutions when, for example, fluorophores are used that result in a signal change as a result of proton exchange.

The analyses may be carried out, for example, directly in body fluids (blood, urine, serum), natural waters or waste water, it being possible for cations that may interfere to be selectively bonded or removed beforehand. The composition according to the invention is suitable especially for determining in aqueous media physiological amounts of cations which, in the case of potassium, for example, may be approximately in the range from 0.5 to 20 mmol.

The ionophores are able to bind both cations and anions.

Cations are, for example, cations of metals from main groups I to V and sub-groups I to VIII of the Periodic Table of the Elements, the lanthanides and actinides. Examples of metals include Li, Na, K, Rb, Cs, Mg, Ca, Sr, Ba, B, Al, Ga, In, Tl, Sn, Pb, Sb, Bi, Cu, Ag, Au, Zn, Cd, Hg, Sc, Y, Ti, Zr, Hf, Cr, Mo, W, Mn, Fe, Co, Ni, Ru, Os, Rh, Ir, Pt, Pd, La, Ce, Pr, Nd, Pm, Sm, Eu, Gd, Tb, Dy, Ho, Er, Yb, Lu, Ac, Th, Pa, U, Np, Pu. Preferred cations are the alkali metal and alkaline earth metal ions, especially $Li^+$, $Na^+$, $K^+$, $Mg^{2+}$, $Ca^{2+}$ and $Sr^{2+}$, and more especially $K^+$, $Na^+$ and $Ca^{2+}$. Suitable ammonium cations are, for example, $NH_4^+$ and the cations of protonated primary, secondary and tertiary amines and of quaternary ammonium. The amines may contain from 1 to 40, especially from 1 to 20 and more especially from 1 to 12, carbon atoms. The quaternary ammonium may contain from 4 to 40, especially from 4 to 20, and more especially from 4 to 16, carbon atoms. Furthermore, organic ions, for example oligoalkylammonium ions, phosphonium ions, guanidine ions or choline ions, may be selectively bonded.

It is possible for anions that are derived from mineral acids, oxyacids and inorganic complex acids to be selectively bound. Examples are the halides and pseudohalides $F^-$, $Cl^-$, $Br^-$, $I^-$, $N_3^-$, $CN^-$, $OCN^-$ and $SCN^-$; anions of the inorganic oxyacids $NO_2^-$, $NO_3^-$, $CO_3^{2-}$, $PO_4^{3-}$, $SO_4^{2-}$, $ClO_4^-$, $MnO_4^-$ and $ClO_3^-$; anions of the inorganic complex acids $Fe(CN)_6^{4-}$ and $Co(CN)_6^{3-}$; the anions of carboxylic acids, phenols; and nucleotide anions, such as adenosine phosphate.

Examples of neutral polar substances that may be selectively bound by the ionophore are urea, thiourea, guanine, guanidine, uric acid, choline, creatinine, amino acids and sugars; being lipophilic molecules, steroids, for example cholesterol, or lipids, for example triglycerides or lecithin, may be selectively bound.

In addition to the preferred fluorescence spectroscopy, other methods of optical measurement may also be used, for example surface plasmon resonance spectroscopy, absorption spectroscopy, reflection spectroscopy, interferometry or surface-enhanced Raman or fluorescence spectroscopy.

The invention relates also to a method for the optical determination of ions in aqueous test samples, in which method a sensor according to the invention is brought into contact with the said aqueous test sample and then the change in fluorescence of the fluorophore in the polymer layer is measured.

The method according to the invention may be carried out, for example, by fixing the carrier with the active polymer layer in an optical cell in which the active layer comes into contact with the test sample. The optical cell has a window through which the active layer can be irradiated for the purpose of excitation and through which the emitted fluorescence radiation can be measured using a spectrofluorometer. The wavelengths may be adjusted to provide maximum absorption for the irradiation and maximum emission for the fluorescence measurement. The intensity is measured as a function of time. The measuring system may be so arranged that the measurement is carried out discontinuously or continuously by, for example, pumping the test solution through the measuring cell. In order to determine unknown concentrations of cations, the system may first be calibrated using test samples of known concentration by plotting the concentrations against the intensity of the fluorescence.

If pH-dependent fluoroionophores are used, it is expedient to add pH buffers to the test sample since, on account of the pH dependency of the absorption spectrum and consequently also the fluorescence intensity of the fluorophore, the sensitivity of the measurement depends on the pH of the test solution. In another embodiment, however, the pH dependency may be determined and taken into account in the calculation. The pH range of the test sample may be, for example, from 4 to 8, preferably from 6.8 to 7.6. Suitable buffers are, for example, citrate buffers and phosphate buffers. Further buffer systems are described in U.S. Pat. No. 4,645,744, especially also those which are directly incorporated in the active layer so as to avoid addition to the test sample.

The invention relates also to the use of the optical sensor for the determination of cations or anions by fluorescence spectroscopy.

The following Examples illustrate the invention.

The following abbreviations are used in the Examples:

h : hours

DMF: dimethylformamide

MS(FD): mass spectrometry (field desorption)

abs.: absorption em.: emission

THF: tetrahydrofuran

MS: mass spectrum

FAB: fast atom bombardment

RT: room temperature

RM: reaction mixture

RPM: revolutions per minute (mm/L): millimol/litre

AIBN: azobisisobutyronitrile $\eta_{inh}$: inherent viscosity

A) Preparation of the Fluoroionophores

EXAMPLE A1

Preparation of Compound A1 a)

[Structure of Compound 5: H₂N-acridine-N(Ts)-propyl-phthalimide]

5

1 g of monotosyl diaminoacridine, 2.21 g of N-(3-bromopropyl)phthalimide (3 equivalents) and 0.54 g of milled KOH (3.5 equivalents) are stirred for 3 days at 50° C. in 15 ml of DMF. The reaction mixture is then poured into water and repeatedly extracted with ethyl acetate. The organic phase is washed with brine, dried and concentrated by evaporation. The crude product is purified over a short column (silica gel, methylene chloride/methanol 8:1). Yield: 1.33 g (88%).

b)

[Structure of Compound 6: H₂N-acridine-N(Ts)-propyl-NH₂]

6

Compound 5 is dissolved in methylene chloride/methanol 2:5 and stirred for 24 h at RT with 7 molar equivalents of hydrazine hydrate. The reaction mixture is poured into 2N HCl, rendered basic and extracted with methylene chloride. The organic phase is washed, dried and concentrated by evaporation. Yield: 26% yellow crystals.

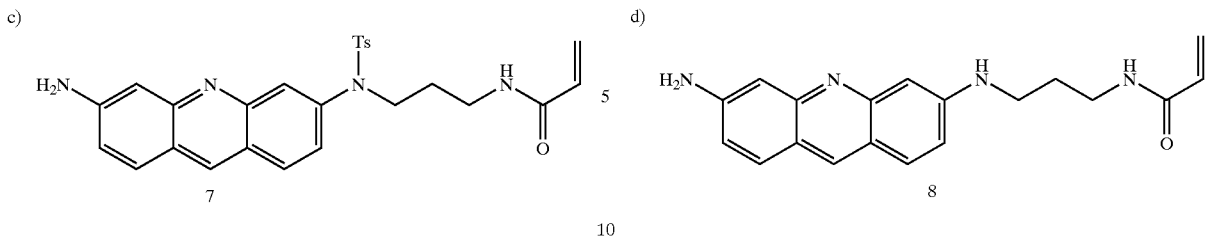

c) Compound 6 and 1.5 equivalents of potassium carbonate are introduced into THF and cooled to −78° C. and 1.5 equivalents of acrylic acid chloride are added. The RM is slowly warmed and is stirred at RT for a further 2 h. The RM is poured into 2N NaOH and extracted with methylene chloride. The organic phase is dried and concentrated by evaporation. The residue is chromatographed on silica gel (methylene chloride/methanol 20:1). Yield: 46% yellow crystals.

d) Compound 8 is stirred for 16 h at RT in a 5:2 mixture of acetic acid/sulfuric acid. The mixture is then poured into 2N NaOH and extracted with ethyl acetate, and the organic phase is back-extracted with brine, dried and concentrated by evaporation. The crude product is used directly in the next Step.

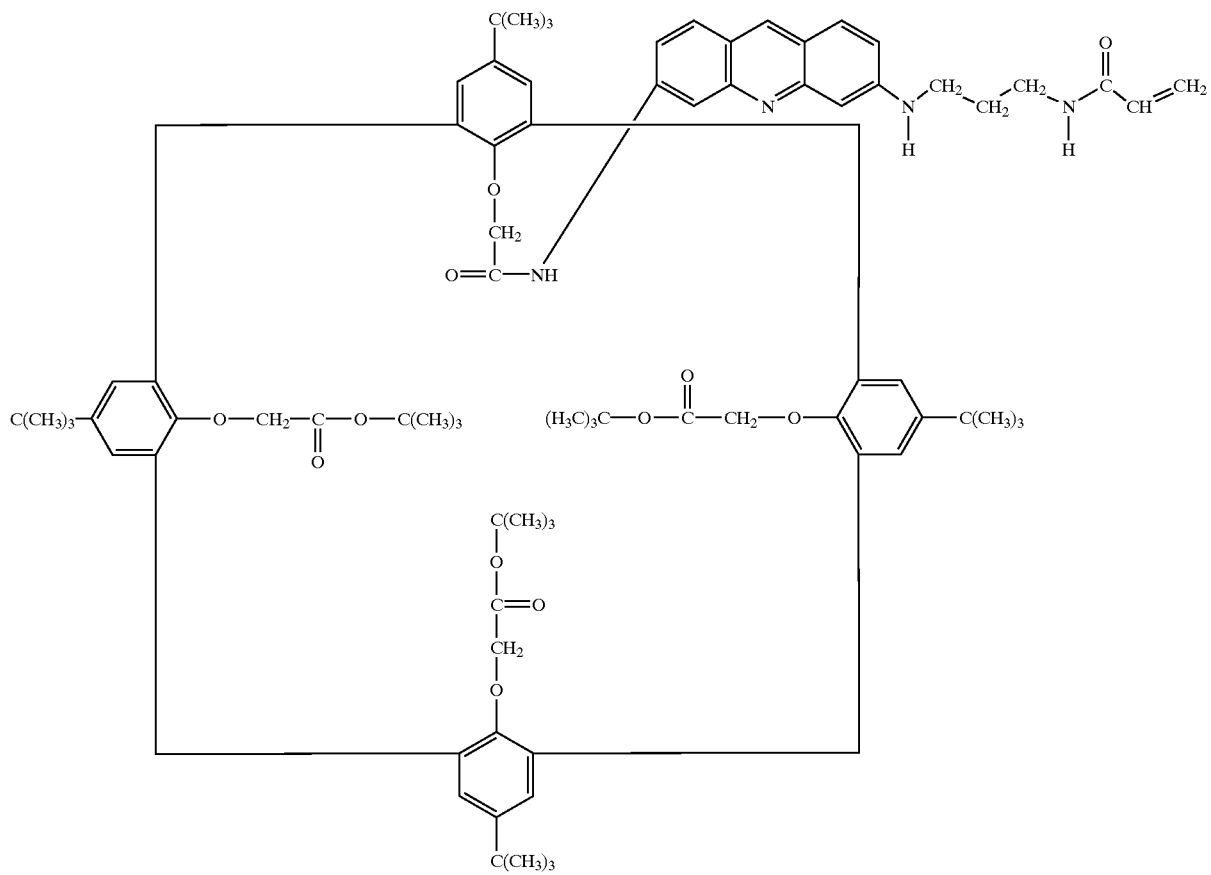

A1

10 molar equivalents of oxalyl chloride are added to calixarene monoacid tri-tert-butyl ester in THF. After 3 h at RT the mixture is concentrated by evaporation and the residue is dried under a high vacuum. The dried residue is dissolved in THF, and 2.2 equivalents of potassium carbonate and 1 equivalent of compound 8 are added. A distinct acceleration of the reaction occurs as a result of the addition of triethylamine. After 16 h at RT the reaction mixture is poured into 2N HCl, the aqueous phase is extracted with ethyl acetate and then the organic phase is washed with brine and dried. After concentration by evaporation a residue remains which is chromatographed on silica gel with methylene chloride/methanol 10:1. Yield : 32%. FAB-MS: 1351 [M+H]⁺; 1373 [M+Na]⁺.

EXAMPLE A2

: Preparation of Compound A2 a)

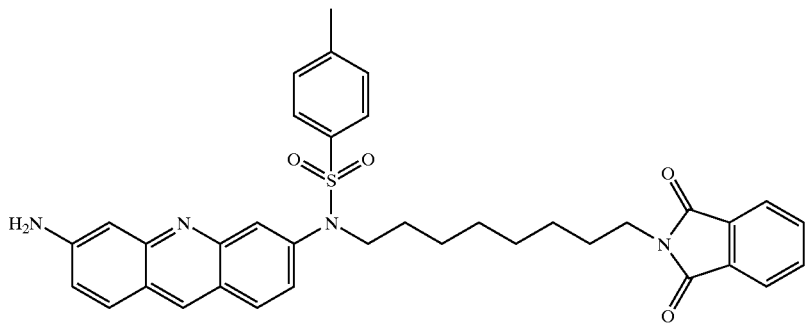

1.8 g of monotosyl diaminoacridine are heated for 4 h at 60° C. with 3 equivalents of N-(8-bromopropyl)phthalimide and 8 equivalents of KOH (milled) in 30 ml of DMF. The reaction mixture is poured into water and extracted twice with ethyl acetate. The organic phase is washed with brine, dried and concentrated by evaporation. Chromatography on silica gel with methylene chloride/methanol 20:1 to 1:1 yields 50% orange, slightly tacky crystals. $^1$H-NMR (CDCl$_3$): 8.55 (s, br., H(9) acridine); 2.40 (s, 3H, CH$_3$).

b)

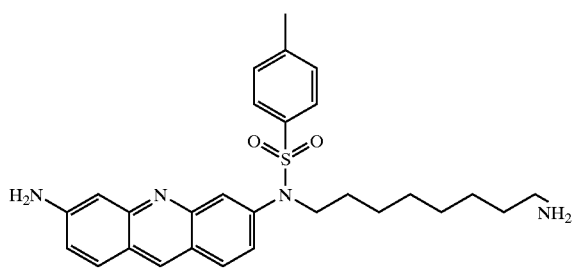

Compound 10 is stirred for 26 h at RT with 7 equivalents of hydrazine hydrate in a mixture of methylene chloride/methanol 2:5. The reaction mixture is diluted with methylene chloride, filtered, and 1N HCl is added. After rendering basic with 2N NaOH, the mixture is extracted with methylene chloride and the organic phase is washed with brine, dried and concentrated by evaporation. The amount of brown residue corresponds to the expected theoretical amount. $^1$H-NMR (CDCl$_3$): 8.55 (s, br., H(9) acridine); 2.40 (s, 3H, CH$_3$).

c)

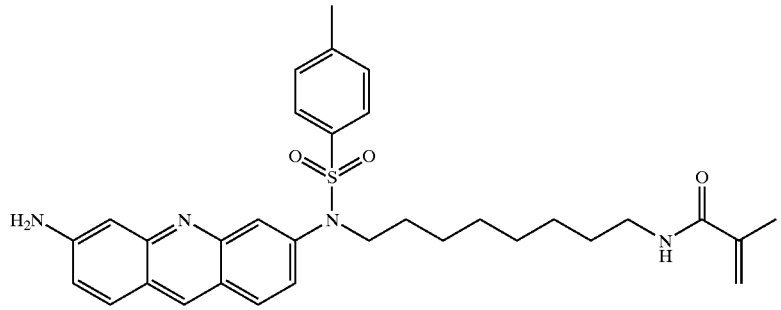

12 lents of potassium carbonate into THF and the mixture is cooled to −78° C. 1 equivalent of methacrylic acid chloride is dissolved in THF and the solution is slowly added dropwise to the above suspension. After allowing to warm up, the reaction mixture is stirred overnight at RT.

The reaction mixture is poured into 2N NaOH and extracted with ethyl acetate. The organic phase is washed with brine, dried and concentrated by evaporation. Purification is carried out by chromatography on silica gel using methylene chloride/methanol 20:1. Yield: 66%. $^1$H-NMR (CDCl$_3$): 8.55 (s, br., H(9) acridine); 5.85 (s, br., NH); 5.66 (m, HC=C); 5.30 (m, HC=C); 2.40 (s, 3H, CH$_3$); 1.95 (m, a s CH$_3$C=C).

d)

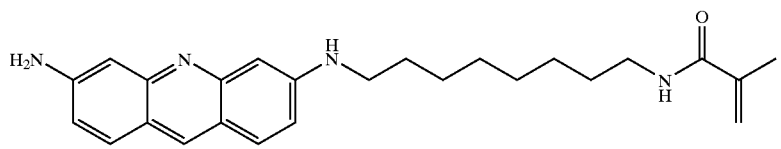

13

Compound 12 is stirred for 16 h at RT in a mixture of acetic acid/sulfuric acid 5:2. The RM is poured into 2N NaOH and extracted with ethyl acetate. The organic phase is washed with brine, dried and concentrated by evaporation. The residue is chromatographed on silica gel with methylene chloride/methanol 9:1 to 4:1 (+5% triethylamine). Yield: 79%. $^1$H-NMR (DMSO-d$_6$): 8.45 (s, br., H(9) acridine); 5.60 (m, HC=C); 5.28 (m, HC=C); 1.85 (m, CH$_3$C=C).

Compound 11 is introduced together with 2 molar equiva e)

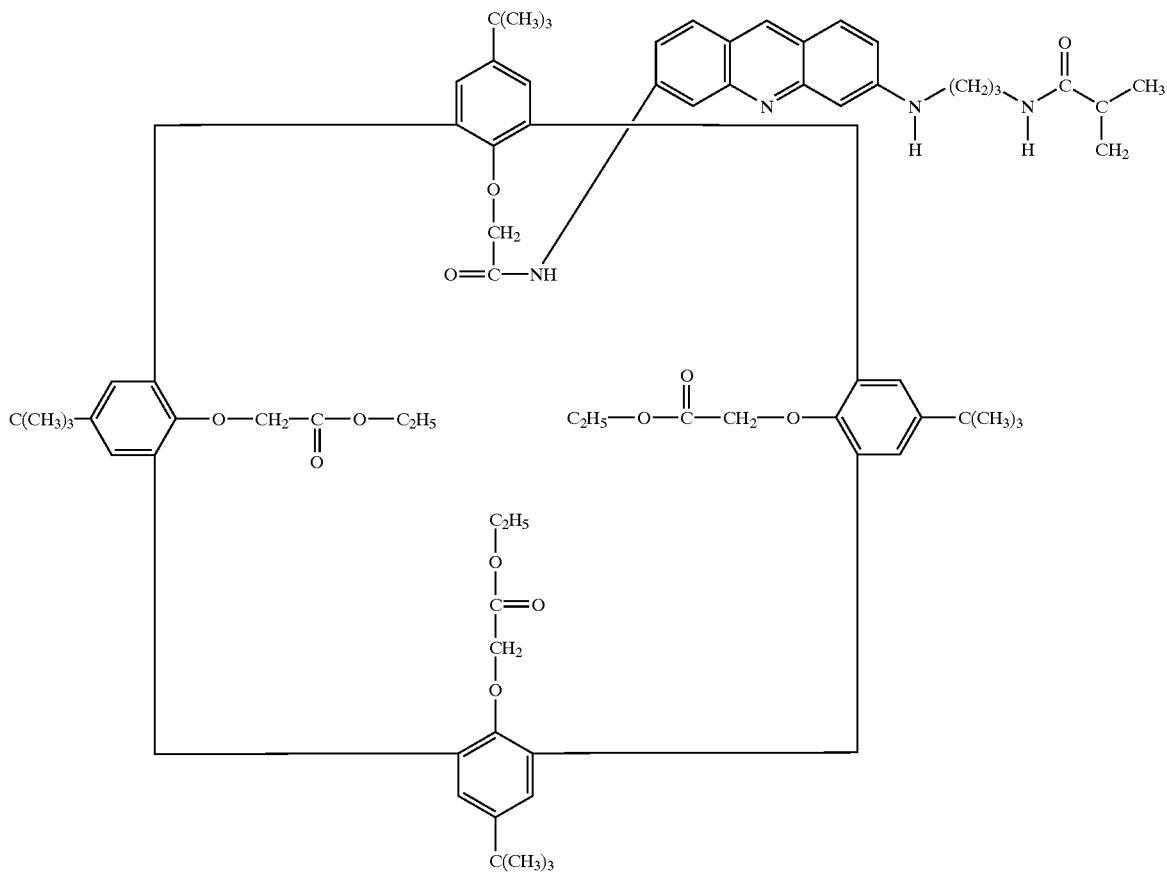

A-2

Calixarene monoacid triethyl ester (0.311 mmol) is heated for 2.5 h at 70° C. in 2 ml of thionyl an chloride and then concentrated by evaporation and dried under a high vacuum. The residue is dissolved in 15 ml of methylene chloride; 4 equivalents of triethylamine and compound 13 are added and the mixture is stirred for 20 h at RT. The reaction mixture is diluted with methylene chloride and washed with 5% acetic acid. The organic phase is washed with saturated hydrogen carbonate solution and water, dried and concentrated by evaporation. Chromatography on silica gel with methylene chloride/methanol 20:1 yields 48% pure product. FAB-MS: 1373 [M+Na]$^+$.

B) Preparation of the Polymer With Covalently Bound Fluoroionophores

EXAMPLE B1

Production of the Sensor With Covalently Bound Fluoroionophores

Preparation of the Polymer B2 Having Fluoroionophore (A2) Incorporated by Polymerisation In a flask fitted with a three-way tap, connected to nitrogen and a vacuum, 1.75 g (17.64 mmol) of N,N-dimethylacrylamide (DMAA), 3.25 g (17.64 mol) of 2-ethyl hexyl acrylate, 35 mg of compound A2 and 25 mg of AIBN are dissolved in 15 ml of dioxane. The air in the flask is replaced by nitrogen in known manner: the contents of the flask are first of all frozen in liquid nitrogen, then a vacuum is applied and the contents are thawed to approximately 0°C., and saturated with gaseous nitrogen. That operation is repeated three times, after which polymerisation is carried out in a water bath of a temperature of 60° C. for 4 days. The polymer solution is diluted with a few ml of dioxane at 50° C. and the polymer is precipitated in 1.5 l of hexane cooled to 4° C., pre-dried in a vacuum drying chamber, and subsequently dried for 48 hours at 50° C. under a high vacuum.

Yield : 3.88g (78% of the theoretical yield), glass transition temperature $T_g$=−10° C. (determined by DSC), inherent viscosity of a 0.5% solution in dioxane at 25° C.: $\eta_{inh}$=0.46 dl/g, the polymer contains 52 mol % DMAA (determined from the elemental analysis).

C) Production of Sensors

Preparation of the polymer Solution 300 mg of copolymer B2 are dissolved in 3 ml of tetrahydrofuran.

Production of the Sensor

200 µl of the polymer solution are applied to a glass substrate having a diameter of 18 mm. The spin-coating is carried out in a first step for 15 seconds at a speed of 8000 RPM and in a second step for 60 seconds at 10 000 RPM. The glass substrate with sensor membrane is stored protected from light, at room temperature, in petri dishes.

D) Application Example

Ion Detection Using the Sensors

Apparatus:

The test apparatus is a conventional fluorescence device. The light beam of a tungsten halogen lamp is used as excitation source and is focused by various lens and filter systems (including a dichroic filter that is set at 45°) onto the sensor surface fixed in a flow cell. The emitted light is focused onto a photodiode detector and the fluorescence intensity is recorded in volts by a computer.

| Measured data: | |
|---|---|
| Sodium ion concentration [mM] | Fluorescence signal [mV] |
| 0 | 498 |
| 1 | 482 |
| 10 | 464 |
| 50 | 437 |
| 100 | 417 |
| 140 | 403 |
| 300 | 385 |
| 500 | 370 |
| 700 | 354 |
| 1000 | 347 |

What is claimed is:

1. A fluoroionophore of the formula

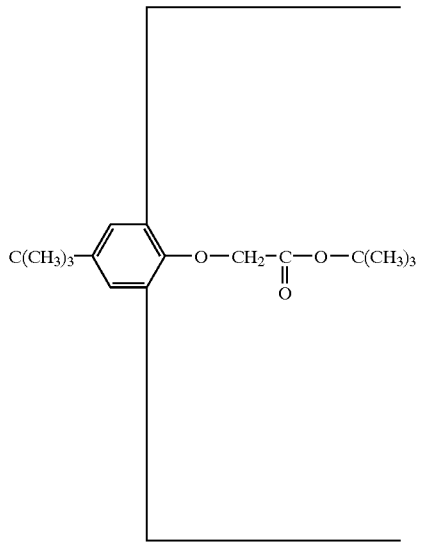

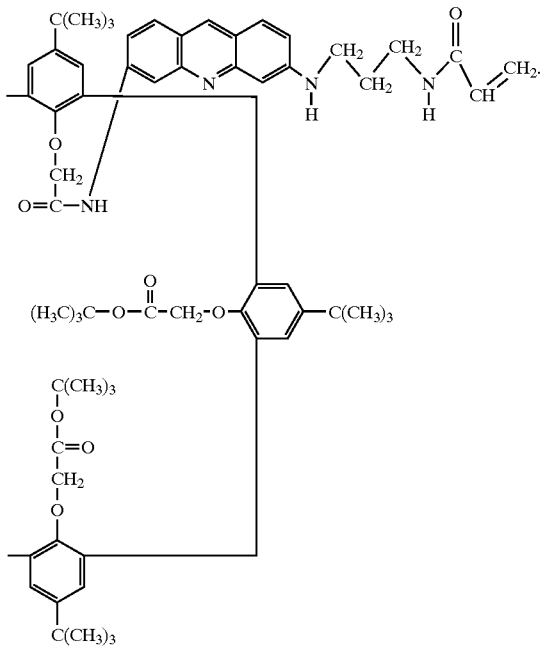

2. A fluoroionophore of the formula
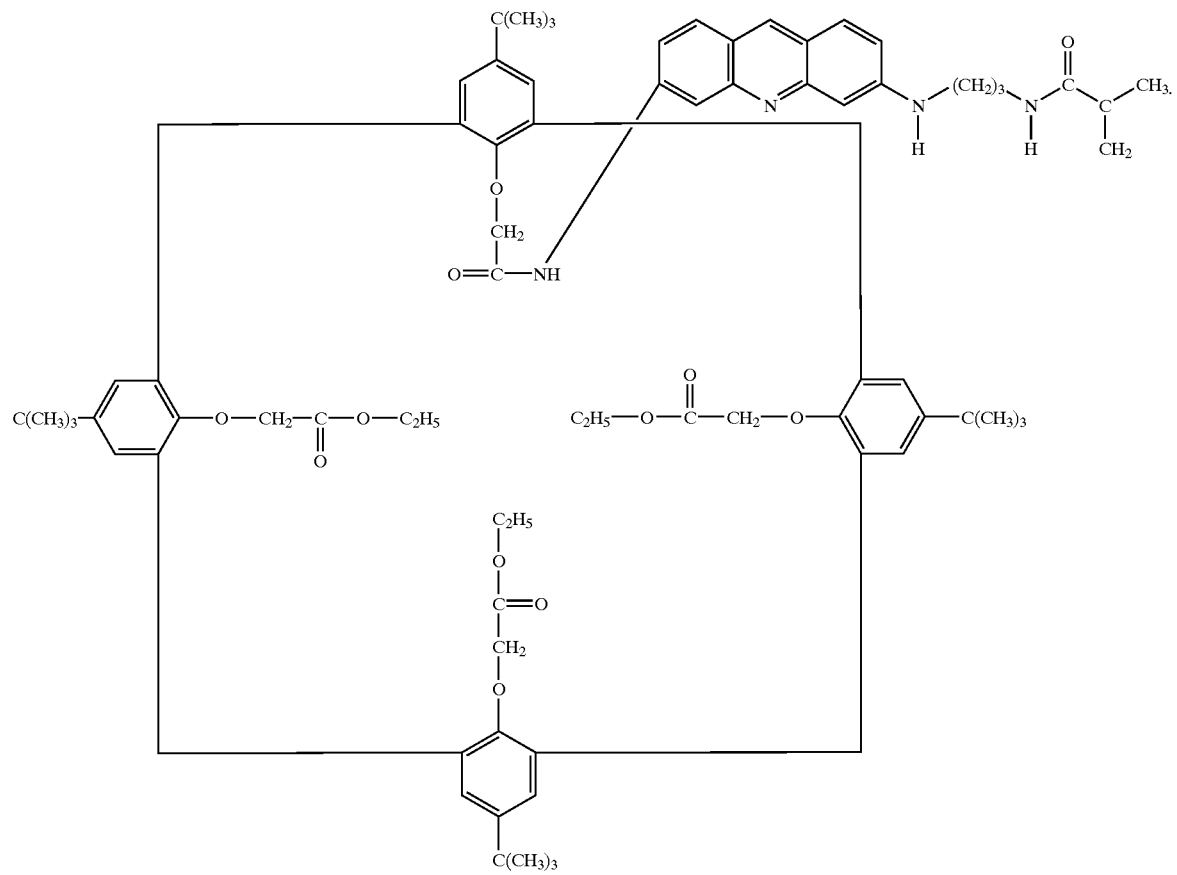

3. A fluoroionophore of the formula

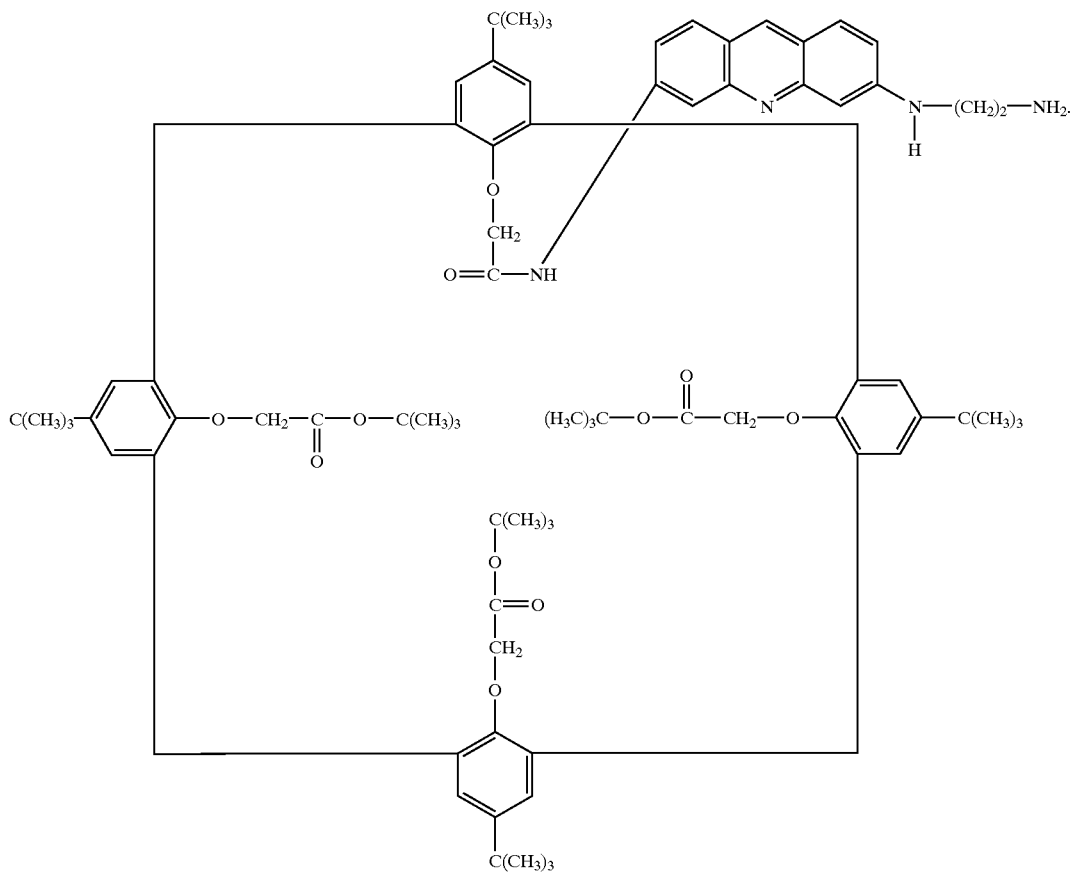

4. A composition comprising (a) an inorganic or organic carrier material to which (b) a fluoroionophore according to any one of claims 1–3 is bonded directly or via a bridging group.

5. A composition according to claim 4, in which the fluoroionophore is covalently bound to the surface of a finely divided carrier material.

6. A composition according to claim 5, wherein there are ionically or covalently bound to the carrier material, in addition, radically or cationically photopolymerisable organic radicals.

7. A composition comprising a natural or synthetic polymer, in which there is incorporated a finely divided inorganic or organic carrier material according to claim 5.

8. A composition according to claim 4, in which the fluoroionophore is covalently bound to a polymer.

9. A composition according to claim 8, wherein the polymer is a polymer having from 100 to 0.001 mol % of identical or different structural units of formula (VII)

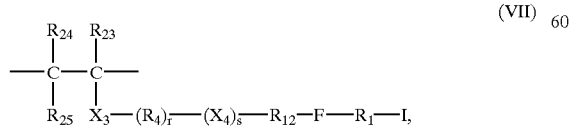
(VII)

and from 0 to 99.9 mol % of identical or different structural units of formula VIII

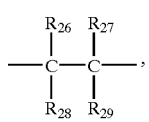
(VIII)

in which formulae
- $X_3$ and $X_4$ are each independently of the other selected from the group consisting of —O—, —S—, —NR$_5$, —C(O)—O—, —O—C(O)—, —O—C(O)—O—, —SO$_2$—O—, —O—SO$_2$—, —O—SO$_2$—O, —NR$_5$—C(O)—, —C(O)—NR$_5$—, —NR$_5$—C(O)—O—, —O—C(O)—NR$_5$—, —NR$_5$—C(O)—NR$_5$—, —NR$_5$SO$_2$—, —SO$_2$—NR$_5$—, —NR$_5$—SO$_2$—O—, —O—SO$_2$NR$_5$- and —NR$_5$SO$_2$—NR$_5$—
- $R_4$ is a divalent bridging group,
- $R_{12}$ is a direct bond, $C_1$-$C_{18}$alkylene, $C_5$- or $C_6$-cycloalkylene, $C_6$-$C_{10}$arylene or $C_7$-$C_{12}$aralkyle r and s are each independently of the others 0 or 1, with the proviso that r or s is 1 when $X_3$ is one of the mentioned groups,
- I is a monovalent residue of an ionophore,
- $R_1$ is a direct bond or a bridging group,
- F is a divalent residue of a fluorophore,
- $R_{23}$ and $R_{24}$ are each independently of the other H, $C_1$-$C_6$alkyl, $C_6$-$C_{10}$aryl or $C_7$-$C_{12}$aralkyl,
- $R_{25}$ is H or the group —C(O)O—R$_{30}$,
- $R_{26}$ is H, $C_1$-$C_6$alkyl, $C_6$-$C_{10}$aryl or $C_7$-$C_{12}$aralkyl, $R_{27}$ is H, F, Cl, CN, $C_1$–$C_6$alkyl or $C_6$–$C_{10}$aryl, $R_{28}$ is H, $C_1$–$C_6$alkyl or —C(O)O—$R_{29}$, $R_{29}$ is H, $C_1$–$C_6$alkyl, $C_6$–$C_{10}$aryl, $C_7$–$C_{12}$ aralkyl, imidazolyl, pyrrolidonyl, F, Cl, CN or the group $X_1$—$(R_1)_r(X_2)_s$—H, and $R_{30}$ is H, K, Na, $C_1$–$C_{18}$alkyl, $C_1$–$C_{18}$hydroxyalkyl, cyclohexyl, cyclopentyl, cyclohexylmethyl, phenyl, $C_1$–$C_4$alkylphenyl, benzyl or $C_1$–$C_4$alkylphenylbenzyl.

10. A composition according to claim 9, wherein the polymer in addition comprises covalently bound radicals of ethylenically unsaturated organic compounds as structural units of formula X

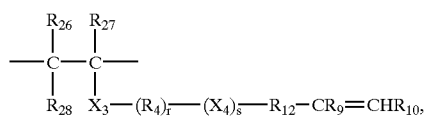

(X)

wherein $R_9$ is H or $C_1$–$C_4$alkyl, especially methyl, $R_{10}$ is H, $C_1$–$C_{12}$alkyl, phenyl or benzyl.

11. A composition according to claim 9, wherein the polymer comprises additional structural units of an at least difunctional monomer as crosslinking agent.

12. A composition according to claim 9, wherein the polymer is an emulsion polymer.

13. A composition comprising a polymer having a covalently bound fluoroionophore according to claim 8, in admixture with a natural or synthetic polymer.

14. A method for the optical determination of ions in aqueous test samples, in which an active layer of a composition according to claim 4 is brought into contact with the aqueous test sample and then the change in fluorescence is measured.

15. A material comprising (a) a support and (b) an active layer on at least one surface, wherein the active layer comprises a fluoroionophore according to any one of claims 1–3 covalently bound to a polymer directly or via a bridging group.

16. A material according to claim 15, wherein the support is transparent.

17. A method for the optical determination of ions in aqueous test samples, in which an active layer of a material according to claim 15 is brought into contact with an aqueous test sample and then the change in fluorescence is measured.

* * * * *